(12) United States Patent
Cooper et al.

(10) Patent No.: US 11,529,421 B2
(45) Date of Patent: Dec. 20, 2022

(54) MODIFIED GLOBIN PROTEINS

(71) Applicant: University of Essex Enterprises Limited, Colchester (GB)

(72) Inventors: Chris E. Cooper, Colchester (GB); Brandon Reeder, Colchester (GB); Gary Silkstone, Colchester (GB)

(73) Assignee: University of Essex Enterprises Limited, Colchester (GB)

( * ) Notice: Subject to any disclaimer, the term of this patent is extended or adjusted under 35 U.S.C. 154(b) by 0 days.

(21) Appl. No.: 15/733,287

(22) PCT Filed: Dec. 19, 2018

(86) PCT No.: PCT/GB2018/053687
§ 371 (c)(1),
(2) Date: Jun. 20, 2020

(87) PCT Pub. No.: WO2019/122871
PCT Pub. Date: Jun. 27, 2019

(65) Prior Publication Data
US 2021/0369851 A1 Dec. 2, 2021

(30) Foreign Application Priority Data
Dec. 20, 2017 (GB) .................... 1721503

(51) Int. Cl.
*A61K 38/42* (2006.01)
*A61K 47/60* (2017.01)
*C07K 14/805* (2006.01)

(52) U.S. Cl.
CPC .............. *A61K 47/60* (2017.08); *A61K 38/42* (2013.01); *C07K 14/805* (2013.01)

(58) Field of Classification Search
CPC ....... A61K 38/42; A61K 47/60; C07K 14/805
See application file for complete search history.

(56) References Cited

U.S. PATENT DOCUMENTS

| | | | | |
|---|---|---|---|---|
| 6,184,356 B1 * | 2/2001 | Anderson | ............... | C12N 15/81 530/402 |
| 6,670,323 B1 * | 12/2003 | Looker | .................... | A61P 7/08 424/85.2 |
| 2005/0227912 A1 * | 10/2005 | Fronticelli | ........... | C07K 14/805 514/13.4 |
| 2009/0215670 A1 * | 8/2009 | Acharya | ............... | C07K 14/805 514/1.1 |

FOREIGN PATENT DOCUMENTS

| | | |
|---|---|---|
| WO | WO-00/18802 A1 | 4/2000 |
| WO | WO-03/008932 A2 | 1/2003 |
| WO | WO-2004063250 A1 | 7/2004 |
| WO | WO-2007050121 A2 | 5/2007 |
| WO | WO-2009004309 A1 | 1/2009 |
| WO | WO-2010/077260 A1 | 7/2010 |
| WO | WO-2014145755 A1 | 9/2014 |
| WO | WO-2018167469 A1 | 9/2018 |
| WO | WO-2019122871 A1 | 6/2019 |

OTHER PUBLICATIONS

Li et al. Molecular Aspects of the High Oxygen Afinity of Non-Hypertensive Hexa Pegylated Hemoglobin, [(SP-PEG5K)6-Hb], Artificial Cells, Blood Substitutes, and Biotechnology. 2007, vol. 35, pp. 19-29. (Year: 2007).*
"International Application No. PCT/GB2018/053687, International Search Report and Written Opinion dated Mar. 15, 2019", (dated Mar. 15, 2019), 11 pgs.
Aich, Anupam, et al., "The free heme concentration in healthy human erythrocytes", Blood Cells, Molecules, and Diseases, vol. 55, Issue 4, Dec. 2015, pp. 402-409, (Sep. 21, 2015), 402-409.
Cheng, Yi, et al., "Ligand Binding Properties and Structural Studies of Recombinant and Chemically Modified Hemoglobins Altered at beta-93 Cysteine", Biochemistry 2002, vol. 41, Issue 39, pp. 11901-11913, (Sep. 7, 2002), 11901-11913.
Kassa, Tigist, et al., "Differential heme release from various hemoglobin redox states and the upregulation of cellular heme oxygenase-1", FEBS Open Bio 6 (2016) 876-884, (2016), 876-884.
Portoro, I., et al., "Towards a novel haemoglobin-based oxygen carrier: Euro-PEG-Hb, physico-chemical properties, vasoactivity and renal filtration", Biochimica et Biophysica Acta 1784 (2008) 1402-1409, (Mar. 20, 2008), 1402-1409.
Ronda, Luca, et al., "Chapter 16—Oxygen Binding to Heme Proteins in Solution, Encapsulated in Silica Gels, and in the Crystalline State", Methods in Enzymology, vol. 437, 2008, pp. 311-328, (Apr. 20, 2008), 311-328.
Saitou, Naruya, et al., "The Neighbor-joining Method: A New Method for Reconstructing Phylogenetic Trees", Molecular Biology and Evolution, vol. 4, Issue 4, Jul. 1987, pp. 406-425, (Jul. 1987), 406-425.
Samaja, Michele, et al., "A new method to measure the haemoglobin oxygen saturation by the oxygen electrode", Journal of Biochemical and Biophysical Methods, vol. 7, Issue 2, Feb. 1983, pp. 143-152, (Jan. 13, 2003), 143-152.
Silkstone, Gary G.A., et al., "Engineering tyrosine electron transfer pathways decreases oxidative toxicity in hemoglobin: implications for blood substitute design", Biochemical Journal, vol. 473, No. 19, epub Jul. 2016, 3371-3383, (Jul. 28, 2016), 3371-3383.
Zheng, Chunyang Y., et al., "Native PAGE eliminates the problem of PEG-SDS interaction in SDS-PAGE and provides an alternative to HPLC in characterization of protein PEGylation", Electrophoresis 2007, 28, 2801-2807, (2007), 2801-2807.

(Continued)

*Primary Examiner* — Jeffrey E. Russel
(74) *Attorney, Agent, or Firm* — Schwegman Lundberg & Woessner, P.A.

(57) ABSTRACT

Certain aspects of the present invention relate to modified hemoglobin proteins comprising at least one modification (e.g., at the thiol group of an exogenous amino acid residue) for homogenous conjugation of one or more polymeric moieties e.g. polyethylene glycol or derivatives thereof. Also included herein are methods of using such modified proteins and compositions comprising such proteins, e.g. in therapy.

19 Claims, 14 Drawing Sheets

Specification includes a Sequence Listing.

(56) References Cited

OTHER PUBLICATIONS

Alayash, Abdu I., "Blood Substitutes: Why Haven't We Been More Successful?", HHS Public Access, published in final edited form as: *Trends Biotechnol.*, 32(4), (2014), 177-185, (2014), 22 pgs.

Chakane, Sandeep, et al., "Fetal hemoglobin is much less prone to DNA cleavage compared to the adult protein", *Redox Biology*, 12, (2017), 114-120.

Coppola, Daniela, et al., "Low affinity PEGylated hemoglobin from *Trematomus bernacchii*, a model for hemoglobin-based blood substitutes", *BMC Biochemistry*, 12, (2011), 8 pgs.

Hu, Tao, et al., "Autoxidation of the Site-Specificallly PEGylated Hemoglobins: Role of the PEG Chains and the Sites of PEGylation in the Autoxidation", *Biochemistry*, 47, (2008), 10981-10990.

Li, Dongxia, et al., "Extension Arm Facilitated Pegylation of αα-Hemoglobin with Modifications Targeted Exclusively to Amino Groups: Functional and Structural Advantages of Free Cys-93(3) in the PEG-Hb Adduct", *Bioconiugate Chem.*, 20, (2009), 2062-2070.

Meng, F., et al., "PEGylation of αα-Hb using succinimidyl propionic acid PEG 5K: Conjugation chemistry and PEG shell structure dictate respectively the oxygen affinity and resuscitation fluid like properties of PEG αα-Hbs", *Artificial Cells Nanomed Technol.*, 43(4), (2015), 270-281.

Olson, John S., et al., "No Scavenging and the Hypertensive Affect of Hemoglobin-based Blood Substitutes", *Free Radical Biology & Medicine*, 36(6), (2004), 685-697.

Prabhakaran, M., et al., "Molecular modeling studies of surface decoration of hemoglobin by maleimide PEG", *Artif Cells Blood Substit Immobil Biotechnol.*, 34(4), (2006), 381-393.

Varnado, Cornelius L., et al., "Development of Recombinant Hemoglobin-Based Oxygen Carriers", *Antioxidants & Redox Signaling*, 18(17), (2013), 2314-2328.

"International Application Serial No. PCT/GB2018/053687, International Preliminary Report on Patentability dated Jul. 2, 2020", 9 pgs.

\* cited by examiner

SEQ ID NO. 1: Human Haemoglobin Beta chain subunit: Wild-Type (WT)

```
         10         20         30         40         50         60
VHLTPEEKSA VTALWGKVNV DEVGGEALGR LLVVYPWTQR FFESFGDLST PDAVMGNPKV
         70         80         90        100        110        120
KAHGKKVLGA FSDGLAHLDN LKGTFATLSE LHCDKLHVDP ENFRLLGNVL VCVLAHHFGK
        130        140
EFTPPVQAAY QKVVAGVANA LAHKYH
```

SEQ ID NO. 2: Human Haemoglobin Alpha chain subunit: Wild-Type (WT)

```
         10         20         30         40         50         60
VLSPADKTNV KAAWGKVGAH AGEYGAEALE RMFLSFPTTK TYFPHFDLSH GSAQVKGHGK
         70         80         90        100        110        120
KVADALTNAV AHVDDMPNAL SALSDLHAHK LRVDPVNFKL LSHCLLVTLA AHLPAEFTPA
        130        140
VHASLDKFLA SVSTVLTSKY R
```

SEQ ID NO. 3: Human Haemoglobin Gamma 1 chain subunit: Wild-type (WT)

```
         10         20         30         40         50         60
GHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKLHVDP ENFKLLGNVL VTVLAIHFGK
        130        140
EFTPEVQASW QKMVTAVASA LSSRYH
```

SEQ ID NO. 4: Human Haemoglobin Gamma 2 chain subunit: Wild-type (WT)

```
         10         20         30         40         50         60
GHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKLHVDP ENFKLLGNVL VTVLAIHFGK
        130        140
EFTPEVQASW QKMVTGVASA LSSRYH
```

FIG. 10

SEQ ID NO. 5: Modified Haemoglobin Alpha chain subunit: A19C

```
         10         20         30         40         50         60
VLSPADKTNV KAAWGKVGCH AGEYGAEALE RMFLSFPTTK TYFPHFDLSH GSAQVKGHGK
         70         80         90        100        110        120
KVADALTNAV AHVDDMPNAL SALSDLHAHK LRVDPVNFKL LSHCLLVTLA AHLPAEFTPA
        130        140
VHASLDKFLA SVSTVLTSKY R
```

SEQ ID NO. 6: Modified Haemoglobin Alpha chain subunit: V1M, A19C, L29F

```
         10         20         30         40         50
MLSPADKTNV KAAWGKVGCH AGEYGAEAFE RMFLSFPTTK TYFPHFDLSH
         60         70         80         90        100
GSAQVKGHGK KVADALTNAV AHVDDMPNAL SALSDLHAHK LRVDPVNFKL
        110        120        130        140
LSHCLLVTLA AHLPAEFTPA VHASLDKFLA SVSTVLTSKY R
```

SEQ ID NO. 7: Modified Haemoglobin Alpha chain subunit: V1M, A19C, L91Y

```
         10         20         30         40         50
MLSPADKTNV KAAWGKVGCH AGEYGAEALE RMFLSFPTTK TYFPHFDLSH
         60         70         80         90        100
GSAQVKGHGK KVADALTNAV AHVDDMPNAL SALSDLHAHK YRVDPVNFKL
        110        120        130        140
LSHCLLVTLA AHLPAEFTPA VHASLDKFLA SVSTVLTSKY R
```

SEQ ID NO. 8: Modified Haemoglobin Beta chain subunit: C93A

```
         10         20         30         40         50         60
VHLTPEEKSA VTALWGKVNV DEVGGEALGR LLVVYPWTQR FFESFGDLST PDAVMGNPKV
         70         80         90        100        110        120
KAHGKKVLGA FSDGLAHLDN LKGTFATLSE LHADKLHVDP ENFRLLGNVL VCVLAHHFGK
        130        140
EFTPPVQAAY QKVVAGVANA LAHKYH
```

FIG. 11

SEQ ID NO. 9: Modified Haemoglobin Beta chain subunit: V1M, V67F, T84Y, C93A

```
            10         20         30         40         50
    MHLTPEEKSA VTALWGKVNV DEVGGEALGR LLVVYPWTQR FFESFGDLST
            60         70         80         90        100
    PDAVMGNPKV KAHGKKFLGA FSDGLAHLDN LKGYFATLSE LHADKLHVDP
           110        120        130        140
    ENFRLLGNVL VCVLAHHFGK EFTPPVQAAY QKVVAGVANA LAHKYH
```

SEQ ID NO. 10: Modified Haemoglobin Gamma 1 chain subunit: C93A

```
            10         20         30         40         50         60
    GHFTEEDKAT ITSLWGKVNV EDAGGETLGR LLVVYPWTQR FFDSFGNLSS ASAIMGNPKV
            70         80         90        100        110        120
    KAHGKKVLTS LGDAIKHLDD LKGTFAQLSE LHADKLHVDP ENFKLLGNVL VTVLAIHFGK
           130        140
    EFTPEVQASW QKMVTAVASA LSSRYH
```

SEQ ID NO. 11: Modified Haemoglobin Gamma 1 chain subunit: G1M, V67F, C93A, L96Y

```
            10         20         30         40         50         60
    MHFTEEDKAT ITSLWGKVNV EDAGGETLGR LLVVYPWTQR FFDSFGNLSS ASAIMGNPKV
            70         80         90        100        110        120
    KAHGKKFLTS LGDAIKHLDD LKGTFAQLSE LHADKYHVDP ENFKLLGNVL VTVLAIHFGK
           130        140
    EFTPEVQASW QKMVTAVASA LSSRYH
```

SEQ ID NO. 12: Modified Haemoglobin Gamma 2 chain subunit: C93A

```
            10         20         30         40         50         60
    GHFTEEDKAT ITSLWGKVNV EDAGGETLGR LLVVYPWTQR FFDSFGNLSS ASAIMGNPKV
            70         80         90        100        110        120
    KAHGKKVLTS LGDAIKHLDD LKGTFAQLSE LHADKLHVDP ENFKLLGNVL VTVLAIHFGK
           130        140
    EFTPEVQASW QKMVTGVASA LSSRYH
```

FIG. 12

SEQ ID NO. 13: Modified Haemoglobin Gamma 2 chain subunit: G1M, V67F, C93A, L96Y

```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKFLTS LGDAIKHLDD LKGTFAQLSE LHADKYHVDP ENFKLLGNVL VTVLAIHFGK
        130        140
EFTPEVQASW QKMVTGVASA LSSRYH
```

SEQ ID NO. 14: Modified Haemoglobin Beta chain subunit: V1M

```
         10         20         30         40         50         60
MHLTPEEKSA VTALWGKVNV DEVGGEALGR LLVVYPWTQR FFESFGDLST PDAVMGNPKV
         70         80         90        100        110        120
KAHGKKVLGA FSDGLAHLDN LKGTFATLSE LHCDKLHVDP ENFRLLGNVL VCVLAHHFGK
        130        140
EFTPPVQAAY QKVVAGVANA LAHKYH
```

SEQ ID NO. 15: Modified Haemoglobin Alpha chain subunit: V1M

```
         10         20         30         40         50         60
MLSPADKTNV KAAWGKVGAH AGEYGAEALE RMFLSFPTTK TYFPHFDLSH GSAQVKGHGK
         70         80         90        100        110        120
KVADALTNAV AHVDDMPNAL SALSDLHAHK LRVDPVNFKL LSHCLLVTLA AHLPAEFTPA
        130        140
VHASLDKFLA SVSTVLTSKY R
```

SEQ ID NO. 16: Modified Haemoglobin Gamma 1 chain subunit: G1M

```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKLHVDP ENFKLLGNVL VTVLAIHFGK
        130        140
EFTPEVQASW QKMVTAVASA LSSRYH
```

FIG. 13

SEQ ID NO. 17: Modified Haemoglobin Gamma 2 chain subunit: G1M

```
         10         20         30         40         50         60
MHFTEEDKAT ITSLWGKVNV EDAGGETLGR LLVVYPWTQR FFDSFGNLSS ASAIMGNPKV
         70         80         90        100        110        120
KAHGKKVLTS LGDAIKHLDD LKGTFAQLSE LHCDKLHVDP ENFKLLGNVL VTVLAIHFGK
        130        140
EFTPEVQASW QKMVTGVASA LSSRYH
```

SEQ ID NO. 18: Modified Haemoglobin Beta chain subunit: A13C, C93A

```
         10         20         30         40         50         60
VHLTPEEKSA VTCLWGKVNV DEVGGEALGR LLVVYPWTQR FFESFGDLST PDAVMGNPKV
         70         80         90        100        110        120
KAHGKKVLGA FSDGLAHLDN LKGTFATLSE LHADKLHVDP ENFRLLGNVL VCVLAHHFGK
        130        140
EFTPPVQAAY QKVVAGVANA LAHKYH
```

FIG. 14

SEQUENCE LISTING

<160> NUMBER OF SEQ ID NOS: 18

<210> SEQ ID NO 1
<211> LENGTH: 146
<212> TYPE: PRT
<213> ORGANISM: Homo sapiens

<400> SEQUENCE: 1

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 2
<211> LENGTH: 141
<212> TYPE: PRT
<213> ORGANISM: Homo sapiens

<400> SEQUENCE: 2

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 3
<211> LENGTH: 146
<212> TYPE: PRT
<213> ORGANISM: Homo sapiens

<400> SEQUENCE: 3

Gly His Phe Thr Glu Glu Asp Lys Ala Thr Ile Thr Ser Leu Trp Gly
1               5                   10                  15

-continued

```
Lys Val Asn Val Glu Asp Ala Gly Gly Glu Thr Leu Gly Arg Leu Leu
            20                  25                  30
Val Val Tyr Pro Trp Thr Gln Arg Phe Phe Asp Ser Phe Gly Asn Leu
        35                  40                  45
Ser Ser Ala Ser Ala Ile Met Gly Asn Pro Lys Val Lys Ala His Gly
    50                  55                  60
Lys Lys Val Leu Thr Ser Leu Gly Asp Ala Ile Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
            100                 105                 110
Val Leu Ala Ile His Phe Gly Lys Glu Phe Thr Pro Glu Val Gln Ala
        115                 120                 125
Ser Trp Gln Lys Met Val Thr Ala Val Ala Ser Ala Leu Ser Ser Arg
    130                 135                 140
Tyr His
145

<210> SEQ ID NO 4
<211> LENGTH: 146
<212> TYPE: PRT
<213> ORGANISM: Homo sapiens

<400> SEQUENCE: 4

Gly His Phe Thr Glu Glu Asp Lys Ala Thr Ile Thr Ser Leu Trp Gly
1               5                   10                  15
Lys Val Asn Val Glu Asp Ala Gly Gly Glu Thr Leu Gly Arg Leu Leu
            20                  25                  30
Val Val Tyr Pro Trp Thr Gln Arg Phe Phe Asp Ser Phe Gly Asn Leu
        35                  40                  45
Ser Ser Ala Ser Ala Ile Met Gly Asn Pro Lys Val Lys Ala His Gly
    50                  55                  60
Lys Lys Val Leu Thr Ser Leu Gly Asp Ala Ile Lys His Leu Asp Asp
65                  70                  75                  80
Leu Lys Gly Thr Phe Ala Gln Leu Ser Glu Leu His Cys Asp Lys Leu
                85                  90                  95
His Val Asp Pro Glu Asn Phe Lys Leu Leu Gly Asn Val Leu Val Thr
            100                 105                 110
Val Leu Ala Ile His Phe Gly Lys Glu Phe Thr Pro Glu Val Gln Ala
        115                 120                 125
Ser Trp Gln Lys Met Val Thr Gly Val Ala Ser Ala Leu Ser Ser Arg
    130                 135                 140
Tyr His
145

<210> SEQ ID NO 5
<211> LENGTH: 141
<212> TYPE: PRT
<213> ORGANISM: Artificial Sequence
<220> FEATURE:
<223> OTHER INFORMATION: Modified Haemoglobin Alpha chain subunit: A19C

<400> SEQUENCE: 5

Val Leu Ser Pro Ala Asp Lys Thr Asn Val Lys Ala Ala Trp Gly Lys
1               5                   10                  15
Val Gly Cys His Ala Gly Glu Tyr Gly Ala Glu Ala Leu Glu Arg Met
```

```
            20                  25                  30
Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140
```

<210> SEQ ID NO 6
<211> LENGTH: 141
<212> TYPE: PRT
<213> ORGANISM: Artificial Sequence
<220> FEATURE:
<223> OTHER INFORMATION: Modified Haemoglobin Alpha chain subunit: V1M,
    A19C, L29F

<400> SEQUENCE: 6

```
Met Leu Ser Pro Ala Asp Lys Thr Asn Val Lys Ala Ala Trp Gly Lys
1               5                   10                  15

Val Gly Cys His Ala Gly Glu Tyr Gly Ala Glu Ala Phe Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140
```

<210> SEQ ID NO 7
<211> LENGTH: 141
<212> TYPE: PRT
<213> ORGANISM: Artificial Sequence
<220> FEATURE:
<223> OTHER INFORMATION: Modified Haemoglobin Alpha chain subunit: V1M,
    A19C, L91Y

<400> SEQUENCE: 7

```
Met Leu Ser Pro Ala Asp Lys Thr Asn Val Lys Ala Ala Trp Gly Lys
1               5                   10                  15

Val Gly Cys His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
```

```
                35                  40                  45
Ser His Gly Ser Ala Gln Val Lys Gly His Gly Lys Lys Val Ala Asp
         50                  55                  60
Ala Leu Thr Asn Ala Val Ala His Val Asp Asp Met Pro Asn Ala Leu
 65                  70                  75                  80
Ser Ala Leu Ser Asp Leu His Ala His Lys Tyr Arg Val Asp Pro Val
                 85                  90                  95
Asn Phe Lys Leu Leu Ser His Cys Leu Leu Val Thr Leu Ala Ala His
            100                 105                 110
Leu Pro Ala Glu Phe Thr Pro Ala Val His Ala Ser Leu Asp Lys Phe
        115                 120                 125
Leu Ala Ser Val Ser Thr Val Leu Thr Ser Lys Tyr Arg
    130                 135                 140

<210> SEQ ID NO 8
<211> LENGTH: 146
<212> TYPE: PRT
<213> ORGANISM: Artificial Sequence
<220> FEATURE:
<223> OTHER INFORMATION: Modified Haemoglobin Beta chain subunit: C93A

<400> SEQUENCE: 8

Val His Leu Thr Pro Glu Glu Lys Ser Ala Val Thr Ala Leu Trp Gly
 1               5                  10                  15
Lys Val Asn Val Asp Glu Val Gly Gly Glu Ala Leu Gly Arg Leu Leu
            20                  25                  30
Val Val Tyr Pro Trp Thr Gln Arg Phe Phe Glu Ser Phe Gly Asp Leu
        35                  40                  45
Ser Thr Pro Asp Ala Val Met Gly Asn Pro Lys Val Lys Ala His Gly
    50                  55                  60
Lys Lys Val Leu Gly Ala Phe Ser Asp Gly Leu Ala His Leu Asp Asn
 65                  70                  75                  80
Leu Lys Gly Thr Phe Ala Thr Leu Ser Glu Leu His Ala Asp Lys Leu
                 85                  90                  95
His Val Asp Pro Glu Asn Phe Arg Leu Leu Gly Asn Val Leu Val Cys
            100                 105                 110
Val Leu Ala His His Phe Gly Lys Glu Phe Thr Pro Pro Val Gln Ala
        115                 120                 125
Ala Tyr Gln Lys Val Val Ala Gly Val Ala Asn Ala Leu Ala His Lys
    130                 135                 140
Tyr His
145

<210> SEQ ID NO 9
<211> LENGTH: 146
<212> TYPE: PRT
<213> ORGANISM: Artificial Sequence
<220> FEATURE:
<223> OTHER INFORMATION: Modified Haemoglobin Beta chain subunit: V1M,
      V67F, T84Y, C93A

<400> SEQUENCE: 9

Met His Leu Thr Pro Glu Glu Lys Ser Ala Val Thr Ala Leu Trp Gly
 1               5                  10                  15
Lys Val Asn Val Asp Glu Val Gly Gly Glu Ala Leu Gly Arg Leu Leu
            20                  25                  30
Val Val Tyr Pro Trp Thr Gln Arg Phe Phe Glu Ser Phe Gly Asp Leu
        35                  40                  45
```

```
Ser Thr Pro Asp Ala Val Met Gly Asn Pro Lys Val Lys Ala His Gly
    50                  55                  60

Lys Lys Phe Leu Gly Ala Phe Ser Asp Gly Leu Ala His Leu Asp Asn
65                  70                  75                  80

Leu Lys Gly Tyr Phe Ala Thr Leu Ser Glu Leu His Ala Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Val Gln Ala
            115                 120                 125

Ala Tyr Gln Lys Val Val Ala Gly Val Ala Asn Ala Leu Ala His Lys
        130                 135                 140

Tyr His
145

<210> SEQ ID NO 10
<211> LENGTH: 146
<212> TYPE: PRT
<213> ORGANISM: Artificial Sequence
<220> FEATURE:
<223> OTHER INFORMATION: Modified Haemoglobin Gamma 1 chain subunit:
      C93A

<400> SEQUENCE: 10

Gly His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
                20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
    50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Ala Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
            115                 120                 125

Ser Trp Gln Lys Met Val Thr Ala Val Ala Ser Ala Leu Ser Ser Arg
        130                 135                 140

Tyr His
145

<210> SEQ ID NO 11
<211> LENGTH: 146
<212> TYPE: PRT
<213> ORGANISM: Artificial Sequence
<220> FEATURE:
<223> OTHER INFORMATION: Modified Haemoglobin Gamma 1 chain subunit:
      G1M, V67F, C93A, L96Y

<400> SEQUENCE: 11

Met His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
                20                  25                  30
```

```
Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
 50                  55                  60

Lys Lys Phe Leu Thr Ser Leu Gly Asp Ala Ile Lys His Leu Asp Asp
 65                  70                  75                  80

Leu Lys Gly Thr Phe Ala Gln Leu Ser Glu Leu His Ala Asp Lys Tyr
                 85                  90                  95

His Val Asp Pro Glu Asn Phe Lys Leu Leu Gly Asn Val Leu Val Thr
                100                 105                 110

Val Leu Ala Ile His Phe Gly Lys Glu Phe Thr Pro Glu Val Gln Ala
                115                 120                 125

Ser Trp Gln Lys Met Val Thr Ala Val Ala Ser Ala Leu Ser Ser Arg
 130                 135                 140

Tyr His
145

<210> SEQ ID NO 12
<211> LENGTH: 146
<212> TYPE: PRT
<213> ORGANISM: Artificial Sequence
<220> FEATURE:
<223> OTHER INFORMATION: Modified Haemoglobin Gamma 2 chain subunit:
      C93A

<400> SEQUENCE: 12

Gly His Phe Thr Glu Glu Asp Lys Ala Thr Ile Thr Ser Leu Trp Gly
  1               5                  10                  15

Lys Val Asn Val Glu Asp Ala Gly Gly Glu Thr Leu Gly Arg Leu Leu
                 20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
 50                  55                  60

Lys Lys Val Leu Thr Ser Leu Gly Asp Ala Ile Lys His Leu Asp Asp
 65                  70                  75                  80

Leu Lys Gly Thr Phe Ala Gln Leu Ser Glu Leu His Ala Asp Lys Leu
                 85                  90                  95

His Val Asp Pro Glu Asn Phe Lys Leu Leu Gly Asn Val Leu Val Thr
                100                 105                 110

Val Leu Ala Ile His Phe Gly Lys Glu Phe Thr Pro Glu Val Gln Ala
                115                 120                 125

Ser Trp Gln Lys Met Val Thr Gly Val Ala Ser Ala Leu Ser Ser Arg
 130                 135                 140

Tyr His
145

<210> SEQ ID NO 13
<211> LENGTH: 146
<212> TYPE: PRT
<213> ORGANISM: Artificial Sequence
<220> FEATURE:
<223> OTHER INFORMATION: Modified Haemoglobin Gamma 2 chain subunit:
      G1M, V67F, C93A, L96Y

<400> SEQUENCE: 13

Met His Phe Thr Glu Glu Asp Lys Ala Thr Ile Thr Ser Leu Trp Gly
  1               5                  10                  15
```

```
Lys Val Asn Val Glu Asp Ala Gly Gly Glu Thr Leu Gly Arg Leu Leu
        20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
    50                  55                  60

Lys Lys Phe Leu Thr Ser Leu Gly Asp Ala Ile Lys His Leu Asp Asp
65                  70                  75                  80

Leu Lys Gly Thr Phe Ala Gln Leu Ser Glu Leu His Ala Asp Lys Tyr
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Gly Val Ala Ser Ala Leu Ser Ser Arg
    130                 135                 140

Tyr His
145

<210> SEQ ID NO 14
<211> LENGTH: 146
<212> TYPE: PRT
<213> ORGANISM: Artificial Sequence
<220> FEATURE:
<223> OTHER INFORMATION: Modified Haemoglobin Beta chain subunit: V1M

<400> SEQUENCE: 14

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
        20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 15
<211> LENGTH: 141
<212> TYPE: PRT
<213> ORGANISM: Artificial Sequence
<220> FEATURE:
<223> OTHER INFORMATION: Modified Haemoglobin Alpha chain subunit: V1M

<400> SEQUENCE: 15

Met Leu Ser Pro Ala Asp Lys Thr Asn Val Lys Ala Ala Trp Gly Lys
```

-continued

```
                1               5                  10                 15
            Val Gly Ala His Ala Gly Glu Tyr Gly Ala Glu Ala Leu Glu Arg Met
                               20                  25                 30
            Phe Leu Ser Phe Pro Thr Thr Lys Thr Tyr Phe Pro His Phe Asp Leu
                               35                  40                 45
            Ser His Gly Ser Ala Gln Val Lys Gly His Gly Lys Lys Val Ala Asp
                  50                   55                   60
            Ala Leu Thr Asn Ala Val Ala His Val Asp Asp Met Pro Asn Ala Leu
             65                   70                   75                  80
            Ser Ala Leu Ser Asp Leu His Ala His Lys Leu Arg Val Asp Pro Val
                               85                   90                  95
            Asn Phe Lys Leu Leu Ser His Cys Leu Leu Val Thr Leu Ala Ala His
                              100                  105                 110
            Leu Pro Ala Glu Phe Thr Pro Ala Val His Ala Ser Leu Asp Lys Phe
                              115                  120                 125
            Leu Ala Ser Val Ser Thr Val Leu Thr Ser Lys Tyr Arg
                  130                  135                  140
```

<210> SEQ ID NO 16
<211> LENGTH: 146
<212> TYPE: PRT
<213> ORGANISM: Artificial Sequence
<220> FEATURE:
<223> OTHER INFORMATION: Modified Haemoglobin Gamma 1 chain subunit: G1M

<400> SEQUENCE: 16

```
            Met His Phe Thr Glu Glu Asp Lys Ala Thr Ile Thr Ser Leu Trp Gly
             1                5                  10                  15
            Lys Val Asn Val Glu Asp Ala Gly Gly Glu Thr Leu Gly Arg Leu Leu
                               20                  25                  30
            Val Val Tyr Pro Trp Thr Gln Arg Phe Phe Asp Ser Phe Gly Asn Leu
                               35                  40                  45
            Ser Ser Ala Ser Ala Ile Met Gly Asn Pro Lys Val Lys Ala His Gly
                  50                   55                   60
            Lys Lys Val Leu Thr Ser Leu Gly Asp Ala Ile Lys His Leu Asp Asp
             65                   70                   75                  80
            Leu Lys Gly Thr Phe Ala Gln Leu Ser Glu Leu His Cys Asp Lys Leu
                               85                  90                   95
            His Val Asp Pro Glu Asn Phe Lys Leu Leu Gly Asn Val Leu Val Thr
                              100                 105                  110
            Val Leu Ala Ile His Phe Gly Lys Glu Phe Thr Pro Glu Val Gln Ala
                              115                 120                  125
            Ser Trp Gln Lys Met Val Thr Ala Val Ala Ser Ala Leu Ser Ser Arg
                  130                  135                  140
            Tyr His
            145
```

<210> SEQ ID NO 17
<211> LENGTH: 146
<212> TYPE: PRT
<213> ORGANISM: Artificial Sequence
<220> FEATURE:
<223> OTHER INFORMATION: Modified Haemoglobin Gamma 2 chain subunit: G1M

<400> SEQUENCE: 17

```
            Met His Phe Thr Glu Glu Asp Lys Ala Thr Ile Thr Ser Leu Trp Gly
             1                5                  10                  15
```

```
Lys Val Asn Val Glu Asp Ala Gly Gly Glu Thr Leu Gly Arg Leu Leu
            20                  25                  30

Val Val Tyr Pro Trp Thr Gln Arg Phe Phe Asp Ser Phe Gly Asn Leu
            35                  40                  45

Ser Ser Ala Ser Ala Ile Met Gly Asn Pro Lys Val Lys Ala His Gly
            50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Cys Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
            115                 120                 125

Ser Trp Gln Lys Met Val Thr Gly Val Ala Ser Ala Leu Ser Ser Arg
            130                 135                 140

Tyr His
145

<210> SEQ ID NO 18
<211> LENGTH: 146
<212> TYPE: PRT
<213> ORGANISM: Artificial Sequence
<220> FEATURE:
<223> OTHER INFORMATION: Modified Haemoglobin Beta chain subunit: A13C,
      C93A

<400> SEQUENCE: 18

Val His Leu Thr Pro Glu Glu Lys Ser Ala Val Thr Cys Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
            50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Ala Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
            130                 135                 140

Tyr His
145
```

MODIFIED GLOBIN PROTEINS

PRIORITY CLAIM TO RELATED APPLICATIONS

This application is a U.S. national stage filing under 35 U.S.C. § 371 from International Application No. PCT/GB2018/053687, filed on 19 Dec. 2018, and published as WO2019/122871 on 27 Jun. 2019, which claims the benefit under 35 U.S.C. § 119 to United Kingdom Application No. GB 1721503.9, filed on 20 Dec. 2017, the benefit of priority of each of which is claimed herein.

FIELD OF THE INVENTION

Certain aspects of the present invention relate to modified proteins e.g. oxygen-carrying proteins, comprising at least one modification for homogenous conjugation of one or more polymeric moieties e.g. polyethylene glycol or derivatives thereof. Also included herein are methods of using such modified proteins and compositions comprising such proteins e.g. in therapy.

BACKGROUND TO THE INVENTION

In cases where major blood loss occurs or blood flow is reduced, such as in cases of where blood flow is reduced due to blood loss due to trauma, disease or ischemia, tissue damage and organ dysfunction can occur due to oxygen deprivation of the cells and tissue leading to hypoxia, anoxia and in some cases cell death.

The use of blood transfusions (red blood cell transfusion) can help transport oxygenated blood through the major blood vessels but not always to smaller capillaries and the microvasculature meaning that these may remain collapsed and in an ischemic condition even after treatment with expanders, drugs or by a blood transfusion.

There also exist a number of issues with red blood cell transfusions. In some cases, blood for use in a red blood cell transfusion may not be readily available such as on the battlefield, in pre-hospital emergency treatment and during major civil crises involving mass casualties. The shelf-life of donated blood and its stringent handling needs also mean that suitable donated blood may not be readily available for transfusion. Issues also arise where patients have rare blood types that are not easily matched or may not accept blood transfusions for religious or personal reasons.

One solution to these problems is the use of a blood substitute. A blood substitute is an oxygen carrying solution that can help to maintain the oncotic pressure needed to maintain blood volume and transport oxygen to cells and tissue around the body therefore helping prevent oxygen deprivation (hypoxia) and ischemia.

Blood substitutes can act as an oxygenation bridge till red blood cell transfusion or in some cases used instead of red blood cell transfusion. It is also possible to use the oxygen carrying constituent of a blood substitute as an oxygen therapeutic. An oxygen therapeutic can be used to help improve the oxygen carrying ability of a patient's blood as well as improving the oxygen carrying capabilities of blood used for transfusions when administered in addition to red blood cells. Oxygen therapeutics as part of a blood substitute or as part of other fluids can be used in a number of methods wherein oxygen may be required such as in the storage of organs as well as in the treatment of carbon monoxide poisoning and in cell culture methods as well.

There are currently two main types of oxygen carrying therapeutics undergoing studies, fluorocarbon emulsions and haemoglobin based oxygen carriers (HBOCs).

Adult haemoglobin in its native environment of a red blood cell is a tetrameric protein composed of two alpha and two beta globin chain subunits, each subunit carrying a haem molecule. One alpha-like globin chain and one beta-like globin chain combine to form a stable dimer. The two dimers are then aligned in an anti-parallel fashion to form a tetramer. The binding between dimers in the tetramer is not as strong as monomers binding to form dimers. Therefore, tetramers have a tendency to dissociate back to dimers. At high globin concentrations, the tetrameric form is the most common but when diluted dimers are the most predominant form. A disadvantage associated with the dimeric form of haemoglobin is that it may lack or have reduced oxygen binding and release kinetics in comparison to the tetrameric form. This may be due to the loss or reduction of cooperative binding of oxygen to the tetrameric form of Haemoglobin.

Another disadvantage associated with the use of native haemoglobin as an oxygen therapeutic is that the tetrameric form readily dissociates into the dimeric form which is rapidly cleared from the blood stream via the kidneys reducing the effectiveness of the HBOC; clearance may also cause damage to the kidneys and renal system.

One method of reducing clearance of exogenous species, such as drugs or proteins, is the addition of Polyethylene Glycol (PEG) chains or other polymers to the surface of an exogenous species. Attachment of PEG may be via covalent or non-covalent bonding of a PEG group to certain reactive groups on a species surface, for example to the R groups of amino acids such as lysine, cysteine, histidine, arginine, aspartic acid, glutamic acid, serine, threonine and/or tyrosine. PEG molecules may also be linked to the N-terminal amino group of a protein or to the C-terminal carboxyl group of a protein. PEG molecules are attached to a species, such as a protein, by PEGylation. PEGylation may be performed using a number of different methods. Generally, there are two main forms of PEGylation, non-specific and specific PEGylation. PEG molecules may be conjugated to different targets through functionalisation of the PEG molecules, to form PEG derivatives with specific chemical reactivity and properties. For example, PEG molecules may be conjugated non-specifically to amine groups using a cyanuric chloride activated PEG molecule or may be more specifically conjugated to amines by the use of PEG-aldehyde derivatives, such as mPEG-propionaldehyde. PEGylation may alternatively involve thiol conjugation through the use of PEG derivatives such as PEG-maleimide, vinylsulfone, iodoacetamide, and orthopyridyl disulphide through formation of thioether or disulphide linkages with amino acid residues such as cysteine. Other PEGylation methods include oxidised carbohydrate and N-terminal conjugation methods, trans-glutamine mediated conjugation methods and click chemistry methods.

PEGylation may alter the hydrodynamic radius and charge properties of a protein, which may help reduce clearance of the protein. PEGylation may also reduce immunogenicity, antigenicity, proteolytic degradation of a protein and increase solubility and stability of a protein.

PEGylation of HBOCs is known but prior art PEGylated HBOCs have often suffered from reduced oxygen transport capabilities such as a lack of binding cooperativity. Prior art PEGylated HBOCs have also been associated with increased haemoglobin dimer formation and reduced tetramer formation, thus, leading to reduced stability of HBOCs and higher levels of haem release from the haemoglobin. Prior art haemoglobin conjugates have also been associated with similar or increased levels of autoxidation in comparison to recombinant and wild type haemoglobins used in blood substitutes.

It is an aim of the present invention to at least partly mitigate the above-mentioned problems.

It is an aim of certain embodiments of the present invention to provide an improved blood substitute.

It is an aim of certain embodiments of the present invention to provide a blood substitute which has a decreased autoxidation rate.

It is an aim of certain embodiments of the present invention to provide a blood substitute which comprises a modified oxygen-carrying protein comprising at least one modification for homogenous conjugation of one or more polymeric moieties with unaltered oxygen carrying capabilities.

It is an aim of certain embodiments of the present invention to provide an improved oxygen therapeutic.

It is an aim of certain embodiments of the present invention to provide an oxygen therapeutic with reduced cytotoxicity.

It is an aim of certain embodiments of the present invention to provide an oxygen therapeutic with increased oxygen carrying capability.

It is an aim of certain embodiments of the present invention to provide an oxygen therapeutic with reduced cytotoxicity and increased oxygen carrying capability.

It is an aim of certain embodiments of the present invention to provide an oxygen therapeutic with increased stability.

It is an aim of certain embodiments of the present invention to provide an oxygen therapeutic with increased stability and increased oxygen carrying capability.

It is an aim of certain embodiments of the present invention to provide an oxygen therapeutic comprising at least one modification for homogenous conjugation of one or more polymeric moieties that does not alter the proteins oxygen carrying capabilities.

It is an aim of certain embodiments of the present invention to provide a PEGylated oxygen therapeutic with unaltered oxygen carrying capabilities.

Summary of Certain Embodiments of the Invention

According to a first aspect of the present invention there is provided a conjugate protein comprising;
a. at least one polymeric moiety; and
b. at least one recombinant modified haemoglobin chain subunit;
wherein the at least one recombinant modified haemoglobin chain subunit comprises at least one modification for introducing at least one exogenous amino acid residue to the at least one recombinant modified haemoglobin chain subunit for conjugation to the at least one polymeric moiety;
and wherein the at least one polymeric moiety is conjugated to the at least one exogenous amino acid residue.

In certain embodiments, the at least one recombinant modified haemoglobin chain subunit comprises at least one or more of an alpha, a beta, a gamma or a delta chain subunit.

In certain embodiments, if the at least one recombinant chain subunit comprises a beta and/or gamma chain subunit, endogenous amino acid residue cysteine 93 is deleted or substituted with an amino acid residue which does not comprise a reactive thiol group. Aptly, the amino acid residue cysteine 93 is substituted with alanine (A), glycine (G), valine (V) or leucine (L). For example, the at least one recombinant chain subunit may comprise:
(i) βC93A, βC93G, βC93V or βC93L;
(ii) γ1C93A, γ1C93G, γ1C93V or γ1C93L; and/or
(iii) γ2C93A, γ2C93G, γ2C93V or γ2C93L.

Aptly, the substitution at amino acid residue cysteine 93 is A.

In certain embodiments, the at least one exogenous amino acid residue comprises at least one reactive thiol group. Aptly, the at least one exogenous amino acid residue comprises cysteine.

In certain embodiments, if the at least one recombinant chain subunit comprises an alpha chain subunit, endogenous amino acid residue alanine 19 is substituted with an amino acid residue comprising at least one reactive thiol group. Aptly, the at least one modification comprises αA19C.

In certain embodiments, the conjugate has at least one substantially unaltered or improved property selected from: at least one oxygen binding property; a rate of oxidation and/or reduction of a haem molecule of the recombinant modified haemoglobin chain subunit; and/or a stability of the recombinant modified haemoglobin chain subunit as compared to a reference protein, wherein said reference protein is a protein comprising the recombinant modified haemoglobin chain subunit without the at least one polymeric moiety.

The terms "conjugate protein" and "conjugate" are used interchangeably herein.

In some embodiments, the at least one oxygen binding property comprises a Hill coefficient of the conjugate. In some embodiments, the at least one oxygen binding property comprises a partial pressure of a gas required to achieve 50% saturation (p50) of the conjugate.

In some embodiments, the rate of oxidation and/or reduction of a haem molecule of the recombinant modified haemoglobin chain subunit is a rate of autoxidation of the haem group of the at least one recombinant modified haemoglobin chain subunit.

In some embodiments, the stability of the at least one recombinant modified haemoglobin chain subunit is measured by a rate of release of the haem molecule from the at least one recombinant modified haemoglobin chain subunit. In some embodiments, the at least one recombinant modified haemoglobin chain subunit is selected from at least one or more of an alpha, a beta, a gamma or a delta chain subunit. In some embodiments, the at least one recombinant modified haemoglobin chain subunit is a mammalian haemoglobin chain subunit.

In certain embodiments, the modification is configured to increase the rate of oxidation of a haem molecule of the recombinant modified haemoglobin chain subunit of no more than about 5% or less as compared to the reference protein.

In some embodiments, the at least one recombinant modified haemoglobin chain subunit is a human haemoglobin chain subunit. In some embodiments, the at least one modification comprises an insertion of the at least one exogenous amino acid residue and/or a substitution of at least one endogenous amino acid residue with the at least exogenous amino acid residue.

In some embodiments, the at least one modification introduces the at least one exogenous amino acid to a position of the at least one recombinant modified haemoglobin chain subunit, wherein the position is located on an outer surface of the conjugate when the conjugate is assembled in a secondary, a tertiary and/or a quaternary structure.

In some embodiments, the at least one modification is configured to provide a conjugation efficiency of at least 30%.

In some embodiments, the at least one reactive thiol group extends outwards from the outer surface of the conjugate when the conjugate is assembled in a secondary, tertiary and/or quaternary structure.

In some embodiments, the at least one exogenous amino acid residue is a cysteine residue.

In some embodiments, the at least one modification is configured to allow conjugation of the at least one polymeric moiety when the at least one recombinant modified haemoglobin chain subunit is in an oxygenated and/or deoxygenated state. In some embodiments, the at least one recombinant modified haemoglobin chain subunit comprises a haemoglobin alpha (α) chain subunit and wherein the at least one modification comprises αA19C. Aptly, the haemoglobin alpha chain subunit is a human mature subunit.

In some embodiments, the conjugate protein further comprises at least one further modification. In some embodiments, the at least one further modification comprises one or more of one or more modifications for decreasing a nitric oxide reactivity; one or more modifications for introducing or enhancing reduction of at least one metallic ion associated with the at least one recombinant modified haemoglobin chain subunit thereby increasing a rate at which an oxidised form of the conjugate is capable of re-oxygenation to an oxygen-binding form; and/or one or more modifications for improving production and/or purification of the at least one recombinant modified haemoglobin chain subunit.

In some embodiments, the at least one recombinant modified haemoglobin chain subunit comprises a haemoglobin alpha chain subunit and wherein the least one further modification is selected from one or more of:
  a. αV1M, αL29F and/or αL91Y.

In some embodiments, the at least one recombinant modified haemoglobin chain subunit is further conjugated to at least one protecting group. In some embodiments, the at least one protecting group is at least one antioxidant enzyme. In some embodiments, the at least one recombinant modified haemoglobin chain subunit comprises an amino acid sequence having at least 80%, e.g. 85%, 90%, 95%, 96, 97, 98 or 99% sequence identity to an amino acid sequence selected from:
  a. SEQ ID NO: 5;
  b. SEQ ID NO: 6 and
  c. SEQ ID NO: 7 and optionally comprises at least modification A19C, and further optionally comprises one or more modifications selected from V1M, L29F and L91Y.

In some embodiments, the at least one polymeric moiety is a non-naturally occurring polymeric moiety. In some embodiments, the at least one polymeric moiety is conjugated to the at least one exogenous amino acid residue via a group selected from at least one maleimide group; at least one vinylsulfone group; at least one thiol group; and/or at least one orthopyridyl disulphide group.

In some embodiments, the at least one polymeric moiety has a molecular weight of about 20,000 Daltons (20 kDa). In some embodiments, the at least one polymeric moiety comprises at least one polyethylene glycol molecule (PEG) or derivative thereof. In some embodiments, the at least one polymeric moiety comprises at least one polyalkylene glycol (PAG) molecule or derivative thereof. In some embodiments, the polymeric moiety is a maleimide functionalized polyethylene glycol.

In some embodiments, the at least one polymeric moiety (e.g. PEG) is homogenously conjugated to the recombinant modified haemoglobin subunit. In other words, a polymeric moiety (e.g. PEG) may be conjugated at a single specific site to the recombinant modified haemoglobin subunit. Advantageously, site-specific conjugation (e.g. PEGylation) enables homogenous (rather than isomeric) conjugates. For example, homogenous conjugation may minimise the effect of conjugation on biological activity of the haemoglobin chain subunit.

In some embodiments, the reference protein comprises an unconjugated form of the at least one recombinant modified haemoglobin chain subunit as described herein.

In some embodiments, the conjugate protein comprises;
  a. at least one polymeric moiety as described herein; and
  b. at least one recombinant modified haemoglobin chain subunit as described herein;
     wherein the at least one recombinant modified haemoglobin chain subunit comprises at least one modification for introducing at least one exogenous amino acid residue to the at least one recombinant modified haemoglobin chain subunit for conjugation to the at least one polymeric moiety; and wherein the at least one polymeric moiety is conjugated to the at least one exogenous amino acid residue; and
  further wherein the conjugate has at least one unaltered or improved property selected from: at least one oxygen binding property; a rate of oxidation and/or reduction of a haem molecule of the recombinant modified haemoglobin chain subunit; and/or a stability of the recombinant modified haemoglobin chain subunit as compared to a reference protein, wherein said reference protein is a protein comprising the recombinant modified haemoglobin chain subunit without the at least one polymeric moiety.

In a further aspect of the present invention, there is provided a recombinant modified multimeric protein comprising at least one conjugate as described herein.

In a further aspect of the present invention, there is provided a recombinant modified multimeric protein comprising;
  a. at least one conjugate as described herein; and
  b. at least one further haemoglobin chain subunit.

In some embodiments, the at least one further haemoglobin chain subunit comprises at least one alpha, at least one beta, at least one delta and/or at least one gamma haemoglobin chain subunit. In some embodiments, the at least one further haemoglobin chain subunit is a mammalian haemoglobin chain subunit. In some embodiments, the at least one further haemoglobin chain subunit is a human haemoglobin chain subunit. In some embodiments, the at least one further haemoglobin chain subunit comprises one or more modifications.

In some embodiments, the one or more modifications are selected from one or more of:
  one or more modifications for decreasing a nitric oxide reactivity;
  one or more modifications for introducing or enhancing reduction of at least one metallic ion associated with the at least one further haemoglobin chain subunit thereby increasing a rate at which an oxidised form of the modified oxygen-carrying conjugate is capable of re-oxygenation to an oxygen-binding form;

one or more modifications for improving production and/or purification of the at least one further haemoglobin chain subunit; and/or one or more modifications for preventing conjugation with the at least one polymeric moiety.

In some embodiments, the at least one further haemoglobin chain subunit is a haemoglobin alpha chain subunit and wherein the one or more modifications are selected from one or more of αV1M, αL29F and αL91Y.

In some embodiments, the at least one further haemoglobin chain subunit is a haemoglobin beta chain subunit and wherein the one or more modifications are selected from one or more of βC93A, βV1M, βV67F, βT84Y, βF85Y and/or βL96Y. In some embodiments, the at least one further haemoglobin chain subunit is a haemoglobin gamma chain subunit and the one or more modifications are selected from one or more of γ1G1M, γ1C93A, γ1L96Y and/or γ1V67F; and/or γ2G1M, γ2C93A, γ2L96Y and/or γ2V67F.

In some embodiments, the at least one further haemoglobin chain subunit is non-conjugated. In some embodiments, the at least one conjugate comprises at least one recombinant modified haemoglobin chain subunit comprising an amino acid sequence having at least about 80% sequence identity to a sequence selected from one or more of: SEQ ID NO: 5; SEQ ID NO: 6; and SEQ ID NO: 7 and wherein, the recombinant modified multimeric protein further comprises at least one further haemoglobin chain subunit comprising an amino acid sequence having at least about 80% e.g. 85%, 90%, 95%, 96%, 97% 98% or 99% sequence identity to a sequence selected from one or more of: SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17 and SEQ. ID. NO. 18.

In some embodiments, the at least one conjugate comprises at least one haemoglobin alpha chain subunit, and wherein the at least one haemoglobin alpha chain subunit comprises the at least one modification αA19C; and further comprises at least one further haemoglobin chain subunit, wherein the at least one further haemoglobin chain subunit comprises at least one haemoglobin beta chain subunit, and wherein the at least one haemoglobin beta chain subunit comprises the modification βC93A.

In some embodiments, the at least one conjugate comprises at least one haemoglobin alpha chain subunit, and wherein the at least one haemoglobin alpha chain subunit comprises the at least one modification αA19C and the further modifications αV1M and αL29F; and further comprises at least one further haemoglobin chain subunit wherein the at least one further haemoglobin chain subunit comprises at least one haemoglobin beta chain subunit, and wherein the at least one beta chain subunit comprises the modifications βC93A, βV1M, βV67F and βT84Y.

In some embodiments, the at least one conjugate comprises at least one haemoglobin alpha chain subunit, and wherein the at least one haemoglobin alpha chain subunit comprises the at least one modification αA19C; and further comprises at least one further haemoglobin chain subunit, and wherein the at least one further haemoglobin chain subunit comprises at least one haemoglobin gamma chain subunit, and wherein the at least one haemoglobin gamma chain subunit comprises the modification γC93A.

In some embodiments, the at least one conjugate comprises at least one haemoglobin alpha chain subunit, and wherein the at least one haemoglobin alpha chain subunit comprises the at least one modification αA19C and the further modifications αV1M and αL29F; and further comprises at least one further haemoglobin chain subunit, wherein the at least one further haemoglobin chain subunit comprises at least one haemoglobin gamma chain subunit, and wherein the at least one haemoglobin gamma chain subunit comprises the modifications γC93A, γG1M, γV67F and γT84Y.

In some embodiments, the at least one conjugate is a first conjugate and the recombinant modified multimeric protein further comprises at least one second conjugate as described herein.

In some embodiments, the at least one further haemoglobin chain subunit is a first haemoglobin chain subunit and the recombinant modified multimeric protein further comprises a second further haemoglobin chain subunit as described herein.

In some embodiments, the multimer is cross-linked. In some embodiments, the reference protein comprises an unconjugated form of the at least one recombinant modified haemoglobin chain subunit as described herein; and further comprises at least one unconjugated form of the further haemoglobin chain subunit as described herein.

In a further aspect of the present invention, there is provided a conjugate as described herein and/or a recombinant modified multimeric protein as described herein for use as a medicament.

In a further aspect of the present invention, there is provided a conjugate as described herein and/or a recombinant modified multimeric protein as described herein for use in the treatment of ischemia and/or hypoxia.

In a further aspect of the present invention, there is provided a composition comprising a conjugate as described herein or a recombinant modified multimeric protein as described herein and a pharmaceutically acceptable carrier or diluent. In some embodiments, the composition further comprises at least one reductant. In some embodiments, the at least one reductant is ascorbate. In some embodiments, the composition is a blood substitute composition.

In a further aspect of the present invention there is provided a composition as described herein for use as a medicament.

In a further aspect of the present invention there is provided a composition as described herein for use as an oxygen therapeutic.

In a further aspect of the present invention there is provided a composition as described herein for use in the treatment of ischemia and/or hypoxia.

In a further aspect of the present invention there is provided a method of treating and/or preventing ischemia and/or hypoxia, the method comprising administering a pharmaceutically effective amount of a pharmaceutical composition as described herein.

Throughout the specification the following abbreviations are used to refer to the described proteins:

A12: HbA comprising the alpha chain modification αA19C and the beta chain modification βC93A; and A13: HbA comprising no alpha chain modifications and the beta chain modifications βA13C and βC93A.

A0: Wild-type native (i.e. not recombinant) HbA;

A1: Wild-type recombinant HbA; and

A11: HbA comprising no alpha chain modifications and the beta chain modification βC93A.

A49: HbA comprising the alpha chain modifications αV1M, αA19C and αL29F and the beta chain modifications βV1M, βV67F, βT84Y and βC93A; and F48: HbF comprising the alpha chain modifications αV1M, αA19C and αL29F and the gamma chain modifications γG1M, γV67F, γL96Y and γC93A.

BRIEF DESCRIPTION OF DRAWINGS

Certain embodiments of the present invention will now be described hereinafter, by way of example only, with reference to the accompanying drawings in which:

FIG. 1 shows (left hand image) SDS-PAGE gel analysis of conjugation products formed, after PEGylation using a 20 kDa maleimide PEG, for adult haemoglobin comprising the alpha chain modification αA19C and the beta chain modification βC93A (referred to as HbA A12 and/or α19C/βC93A)) and SDS-PAGE gel analysis (FIG. 1, right hand image) of recombinant wild-type adult haemoglobin (referred to as A1). FIG. 1, column 1, contains molecular weight markers, column 2 contains un-conjugated HbA A12 and column 3 contains conjugated HbA A12. It can be seen in column 3 that only one species (1P) having a molecular weight greater than the dimer alone (D) was seen after conjugation. The single band at approximately 60 kDa (1P) indicates a homogenously PEGylated alpha subunit (i.e. a single PEG molecule conjugated to the α-chain subunit via the cysteine residue introduced by the modification αA19C). The higher apparent molecular mass of alpha-PEG conjugate is due to well documented PEG-SDS interaction (Zheng C, Ma G and Su Z. *Electrophoresis.* (2007) 28, 2801-2807). A band corresponding to unconjugated monomeric α and β chain subunits (M) and a band corresponding to un-PEGylated alpha and beta chain subunit dimers (D) can also be seen. FIG. 1 (right hand image) shows SDS-PAGE analysis of HbA A1 PEGylated using a 5.6 kDa maleimide PEG conjugated via non-specially formed thiol groups located on surface lysine residues (prior art method: see Portoro, I., Kocsis, L., Herman, P., Caccia, D., Perrella, M., Ronda, L., Bruno, S., Bettati, S., Micalella, C., Mozzarelli, A., Varga, A., Vas, M., Lowe, K. C., and Eke, A. (2008) *Biochim. Biophys. Acta* 1784, 1402-1409). Column 1 contains molecular weight markers, column 2 contains un-conjugated HbA A1 and column 3 contains conjugated HbA A1. A number of bands can be seen on the gel (1P to 8P) in column 3 each band corresponding to a number of species conjugated to multiple PEG moieties. The band labelled M corresponds to unconjugated monomeric α and β chain subunits.

FIG. 3 shows size exclusion chromatography (SEC) analysis of undenatured Hb variants unconjugated (left hand image) and conjugated to maleimide PEG 20 kDa (right hand image). The peak seen at 7.7 min corresponds to homogenously PEGylated protein. A12 has fewer peaks at different timepoints, whereas A1 and A13 both have a greater number of peaks including a large peak at 10.9 min that correspond to un-PEGylated protein. This indicates that A12 forms a greater amount of homogenously conjugated dimer;

FIG. 4 shows SDS-PAGE gels comparing the efficiency of conjugation at different PEG concentrations and time points (at room temperature) for A12. It can be seen from the intensity of the bands (as determined by densitometry) indicated on the gels that the greatest amount of PEGylation efficiency is seen at a ratio of 12:1 PEG to protein (i.e. a 12-fold excess of PEG) and an incubation time of 3-4 hours. However, even at PEG:Hb ratios as low as 3:1, a third of the HbA is PEGylated successfully. It is noted that the "perfect" homogenous product would be 50% free β subunit at 17 kDa and 50% α-PEG subunit at 50 kDa;

FIG. 10 illustrates the amino acid sequences of:
wild-type human haemoglobin beta chain subunit (SEQ. ID. NO. 1);
wild-type human haemoglobin alpha chain subunit (SEQ. ID. NO. 2);
wild-type human haemoglobin gamma 1 chain subunit (also known as gammaA) (SEQ. ID. NO. 3);
wild-type human haemoglobin gamma 2 chain subunit (also known as gammaG) (SEQ. ID. NO. 4); and
haemoglobin alpha chain with the modification A19C (SEQ. ID. NO. 5);

FIG. 11 illustrates the amino acid sequences of:
haemoglobin alpha chain with the modifications V1M, A19C and L29F (SEQ. ID. NO. 6);
haemoglobin alpha chain with the modifications V1M, A19C and L91Y (SEQ. ID. NO. 7); and
haemoglobin beta chain with the modification C93A (SEQ. ID. NO. 8);

FIG. 12 illustrates the amino acid sequences of:
haemoglobin beta chain with the modifications V1M, V67F, T84Y and C93A (SEQ. ID. NO. 9);
haemoglobin gamma 1 chain with the modification C93A (SEQ. ID. NO. 10);
haemoglobin gamma 1 chain with the modifications G1M, V67F, C93A and L96Y (SEQ. ID. NO. 11); and
haemoglobin gamma 2 chain with the modification C93A (SEQ. ID. NO. 12);

FIG. 13 illustrates the amino acid sequences of:
haemoglobin gamma 2 chain with the modifications G1M, V67F, C93A and L96Y (SEQ. ID. NO. 13);
haemoglobin beta chain with the modification V1M (SEQ. ID. NO. 14);
haemoglobin alpha chain with the modification V1M (SEQ. ID. NO. 15); and
haemoglobin gamma 1 chain with the modification G1M (SEQ. ID. NO. 16); and FIG. 14 illustrates the amino acid sequences of:
haemoglobin gamma 2 chain with the modification G1M (SEQ. ID. NO. 17); and
haemoglobin beta chain with the modifications A13C and C93A (SEQ. ID. NO. 18).

DETAILED DESCRIPTION OF CERTAIN EMBODIMENTS

Figure 1:
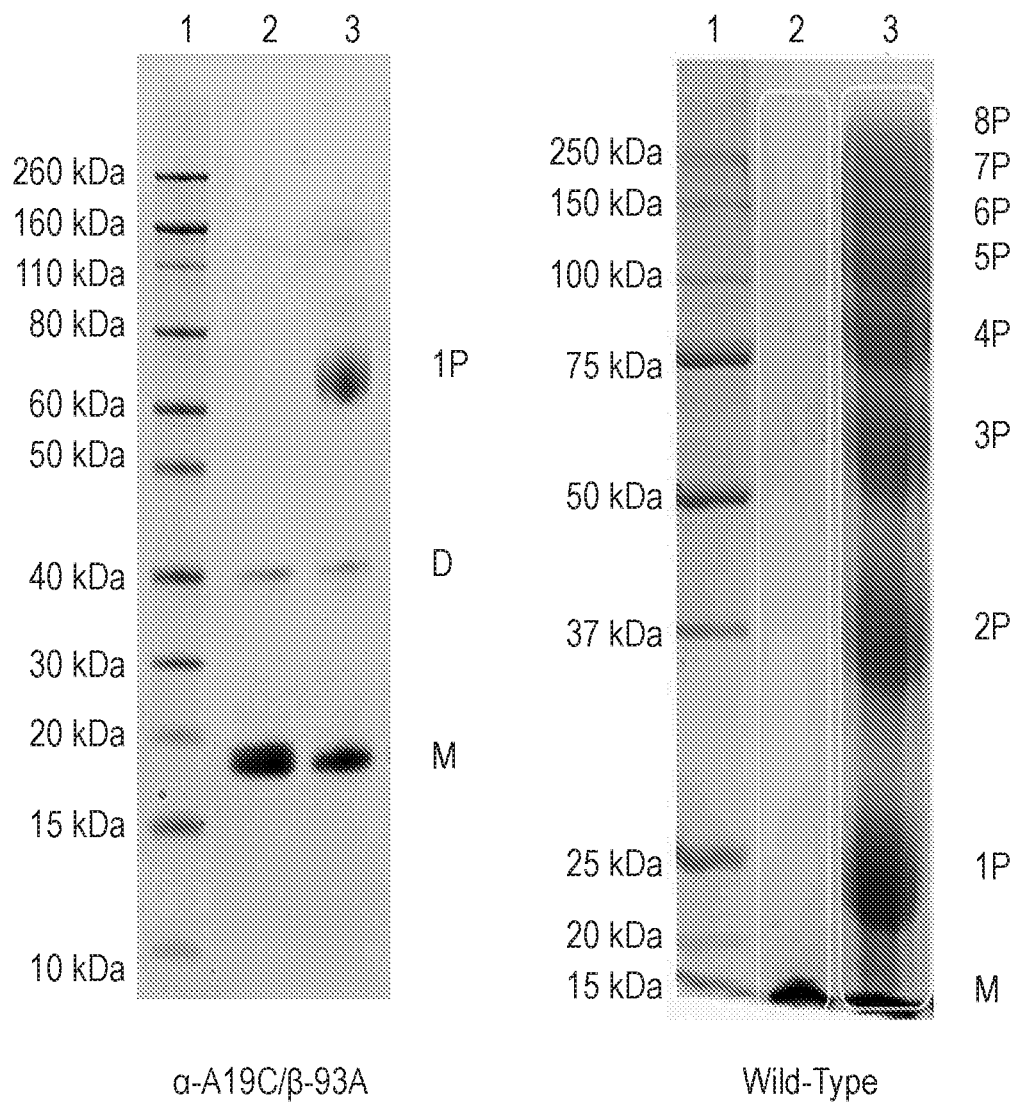
FIGS. 1-4 describe maleimide-PEGylation to the carbon monoxide bound form of the protein. This is in the same conformational state (R) as oxygenated haemoglobin.

Further features of certain embodiments of the present invention are described below.

The practice of embodiments of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, $2^{nd}$ ed., 2002, CRC Press; The Dictionary of Cell and Molecular Biology, $3^{rd}$ ed., Academic Press; and the Oxford University Press, provide a person skilled in the art with a general dictionary of many of the terms used in this disclosure.

Units, prefixes and symbols are denoted in their Systeme International de Unitese (SI) accepted form. Numeric ranges are inclusive of the numbers defining the range. Unless otherwise indicated, amino acid sequences are written left to right in amino to carboxy orientation. All amino acid residues in proteins of embodiments of the invention are preferably of the L-configuration. However, D-configuration amino acids may also be present. Throughout this specification, the conventional one letter and three letter codes for naturally occurring amino acids are used, as well as generally accepted three letter codes for other amino acids.

Certain embodiments of the present invention relate to conjugates which may be considered as comprising oxygen-carrying proteins. As used herein the term "oxygen-carrying protein" refers to any polypeptide chain that in its native state is able, alone or in complex with other molecules (for example haem) and/or polypeptides, to bind to oxygen, transport oxygen and subsequently release oxygen bound to the protein, therefore is a polypeptide that reversibly binds to oxygen. Oxygen-carrying proteins that may be modified as is disclosed herein may be recombinant proteins as well as any synthetically engineered proteins where the protein has been engineered so as to reversibly bind oxygen. In some embodiments, the protein is an isolated, recombinant, substantially pure, or non-naturally occurring oxygen-carrying protein.

As used herein the terms "polypeptide" and "protein" are terms that are used interchangeably to refer to a polymer of amino acids, without regard to the length of the polymer. Typically, polypeptides and proteins have a polymer length that is greater than that of "peptides."

As used herein, the term "native wild-type" refers to an amino acid sequence or nucleic acid sequence that is a naturally-occurring sequence. As used herein, the term "naturally-occurring" refers to anything (e.g., proteins, amino acids, or nucleic acid sequences) that are found in nature and may subsequently be isolated from their natural environment. For example, native wild-type human HbA may be isolated from a human red blood cell. Conversely, the term "non-naturally occurring" refers to anything that is not found in nature (e.g., recombinant nucleic acids and protein sequences produced in the laboratory or modifications of the wild-type sequence). Thus, as used herein, the term "recombinant wild-type (rWT)" refers to an amino acid or nucleic acid sequence that has the same amino acid residue or nucleotide sequence as the corresponding native wild-type but is produced using recombinant techniques. In certain embodiments, native wild-type protein and/or recombinant wild-type protein is a human haemoglobin beta chain subunit as set forth in SEQ. ID. No. 1. In certain embodiments, native wild-type protein and/or recombinant wild-type protein is a human haemoglobin alpha chain subunit as set forth in SEQ. ID. No. 2. In certain embodiments, native wild-type protein and/or recombinant wild-type protein is a human haemoglobin gamma 1 chain subunit (also known as gamma-A) as set forth in SEQ. ID. No. 3. In certain embodiments, the native wild-type protein and/or recombinant wild-type protein is a human haemoglobin gamma 2 chain subunit (also known as gamma-G) as set forth in SEQ. ID. No. 4.

The numbering used for modifications of certain embodiments of the present invention, refers to the amino acid residue positions with reference to the wild-type mature human haemoglobin beta, alpha, gamma 1 and/or gamma 2 chain subunit amino acid sequences as set forth in SEQ. ID. NO. 1, SEQ. ID. NO. 2, SEQ. ID. NO. 3 and/or SEQ. ID. NO. 4 respectively. It will be understood by those skilled in the art that in certain embodiments wherein the conjugate protein comprises further modifications such as deletions or insertions the numbering of the above-mentioned modifications will change.

As used herein, the terms "modified" and "modification" refer to substitution, addition or deletion of an amino acid residue or amino acid residues, and includes substitutions with or additions of any of the 20 amino acids commonly found in human proteins, as well as atypical or non-naturally occurring amino acids.

The term "isolated" as used herein refers to a protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In certain embodiments, the protein is purified:
  (1) to a degree sufficient to obtain at least 15 residues of N-terminal or internal amino acid sequence by use of a spinning cup sequenator; or
  (2) to homogeneity by SDS-PAGE under non-reducing or reducing conditions using Coomassie blue or silver stain.

Recombinant Modified Haemoglobin Chain Subunits

In one aspect of the present invention there is provided, a conjugate protein comprising;
  a. at least one polymeric moiety; and
  b. at least one recombinant modified haemoglobin chain subunit comprising at least one or more of an alpha, a beta, a gamma or a delta chain subunit;
    wherein the at least one recombinant modified haemoglobin chain subunit comprises at least one modification for introducing at least one exogenous amino acid residue comprising at least one reactive thiol group to the at least one recombinant modified haemoglobin chain subunit for conjugation to the at least one polymeric moiety;
    wherein the at least one polymeric moiety is conjugated to the at least one exogenous amino acid residue; and
    wherein, if the at least one recombinant chain subunit comprises a beta and/or a gamma chain subunit, endogenous amino acid residue cysteine 93 is deleted or substituted with an amino acid residue which does not comprise a reactive thiol group.

In certain embodiments, the conjugate has at least one unaltered or improved property selected from: at least one oxygen binding property; a rate of oxidation and/or reduction of a haem molecule of the haemoglobin chain subunit; and/or a stability of the haemoglobin chain subunit as compared to a reference protein, wherein said reference protein is a protein comprising the recombinant modified haemoglobin chain subunit without the at least one polymeric moiety.

As described herein, the conjugate protein comprises at least one recombinant modified haemoglobin chain subunit. Haemoglobins are tetrameric proteins made up of four polypeptide subunits each of which comprise a haem molecule. Haemoglobins constitute the oxygen carrying component of blood contained within red blood cells. In the absence of oxygen haemoglobin with its haem cofactor in the ferrous oxidation state is termed deoxyhaemoglobin. As blood circulates through the lungs, the oxygen present in the alveolar capillaries diffuses through the alveolar membrane and acts to convert haemoglobin within the red blood cells to a reversible molecular complex known as oxyhaemoglobin. Because the association of the oxygen and haemoglobin is reversible, the oxygen molecules are gradually released from the haemoglobin when blood reaches the tissue capillaries. Eventually, the oxygen molecules diffuse into the tissues and are consumed by metabolism. As the oxygen is released, oxyhaemoglobin is converted back to deoxyhaemoglobin.

In certain embodiments, the at least one recombinant modified haemoglobin chain subunit is derived from a vertebrate haemoglobin. In certain embodiments, the at least one recombinant modified haemoglobin chain subunit is a mammalian haemoglobin chain subunit. In certain embodiments, the at least one recombinant modified haemoglobin chain subunit is a human haemoglobin chain subunit.

In certain embodiments, the at least one haemoglobin subunit is a member of the alpha chain superfamily. As defined herein the term "superfamily" refers to proteins that may have low sequence identities but whose structural and functional features suggest that the proteins share a common evolutionary origin. By way of example the at least one recombinant modified haemoglobin chain subunit may be selected from at least one of a beta, an alpha, a gamma 1, a gamma 2, a delta, a zeta or an epsilon haemoglobin chain subunit.

In certain embodiments, the at least one recombinant modified haemoglobin chain subunit is a haemoglobin alpha chain subunit.

In certain embodiments, the recombinant modified haemoglobin chain subunit is a human haemoglobin alpha chain subunit.

In certain embodiments, the at least one recombinant modified haemoglobin chain subunit is a human haemoglobin beta chain subunit. In certain embodiments, the at least one recombinant modified haemoglobin chain subunit is a human haemoglobin gamma chain subunit. In certain embodiments, the at least one recombinant modified haemoglobin chain subunit is a human haemoglobin gamma 1 chain subunit. In certain embodiments, the at least one recombinant modified haemoglobin chain subunit is a human haemoglobin gamma 2 chain subunit.

In certain embodiments, the at least one recombinant modified haemoglobin chain subunit may be a homologue of a haemoglobin alpha chain subunit. As used herein the term "homologous proteins" and "homologue" refer to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST. Using this information, protein sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can help reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions.

Modifications

In certain embodiments, the at least one modification comprises an insertion of at least one exogenous amino acid residue and/or a substitution of at least one endogenous amino acid residue with the at least exogenous amino acid residue. Aptly, the at least one modification is an insertion of at least one exogenous amino acid residue. Aptly, the at least one modification is a substitution of at least one endogenous amino acid residue of the at least one recombinant haemoglobin chain subunit with an exogenous amino acid residue.

In certain embodiments, the at least one modification introduces the at least one exogenous amino acid to a position of the at least one recombinant modified haemoglobin chain subunit, wherein the position is located on an outer surface of the conjugate when the conjugate is assembled in a secondary, a tertiary and/or a quaternary structure.

As used herein the term "the outer surface" of the conjugate refers to a surface of the conjugate that is contactable with reactants, such a polymeric moiety as described herein, and able to undergo reactions such as a conjugation reaction.

Without being bound by theory, a suitable position for the at least one modification may be determined by, but not limited to, analysis of the three-dimensional structure of a haemoglobin chain subunit and/or haemoglobin dimer and/or tetramer using three dimensional structures determined by methods such as x-ray crystallography or nuclear magnetic resonance imaging. Positioning the at least one modification on an outer surface of a haemoglobin chain subunit when in assembled in a secondary, a tertiary and/or a quaternary structure may help reduce the likelihood of the at least one modification having detrimental effect on assembly of the protein into high order structures such as dimers, trimers or tetramers. Moreover, positioning the at least one modification on an outer surface reduces the likelihood of altering binding of the haem group of the at least one haemoglobin chain subunit and/or altering binding of oxygen to the haem group.

In certain embodiments, the at least one modification is configured to provide a conjugation efficiency of at least 10%. Aptly, at least 20%. Aptly at least 30%. Aptly at least 40%.

In certain embodiments, the at least one modification is configured to provide a conjugation efficiency of at least 30%.

Conjugation efficiency may be determined by measuring the ratio of haemoglobin chain subunits conjugated to the at least one polymeric memory to the total number of haemoglobin chain subunits subjected to a conjugation reaction. Methods of determining the ratio of conjugated haemoglobin chain subunit to total number of haemoglobin chain subunits may include but are not limited to SDS-PAGE gel separation of products formed by a conjugation reaction and analysis of concentrations of different species formed using for example densitometry and/or size exclusion chromatography (SEC).

In certain embodiments, the at least one exogenous amino acid residue comprises at least one reactive thiol group. As used herein the term "reactive thiol group" refers to a functional group containing a sulphur atom bonded to a hydrogen atom with the general formula —SH that is capable of undergoing chemical reactions for example, conjugation to a polymeric moiety as described herein.

In certain embodiments, the at least one reactive thiol group extends outwards from the outer surface of the conjugate when the conjugate is assembled in a secondary, a tertiary and/or a quaternary structure.

Without being bound by theory, a reactive thiol group which extends outwards from the outer surface of the conjugate will be readily accessible to reactants, such as polymeric moieties, and therefore help provide a higher conjugation efficiency. It also may help reduce detrimental effects on properties of the conjugate such as reduced oxygen binding properties and/or stability which may be caused by conjugation of the at least one polymeric moiety at a location that interferes with the folding or assembly of multimers or conformational changes that may occur upon binding of oxygen by the haemoglobin chain subunit.

The at least one exogenous amino acid residue may be any naturally occurring or non-naturally occurring amino acid residue comprising a free thiol group.

In certain embodiments, the at least one exogenous amino acid residue is a cysteine residue.

In certain embodiments the at least one modification is configured to allow conjugation of the at least one polymeric moiety when the at least one recombinant modified haemoglobin chain subunit is in an oxygenated (also referred to as Relaxed (IR)-state) and/or deoxygenated state (also referred to as tense (T)-state).

In certain embodiments, wherein the at least one recombinant modified haemoglobin chain subunit comprises a haemoglobin alpha (a) chain subunit the at least one modification comprises the modification αA19C.

In certain embodiments, the conjugate further comprises at least one further modification.

In certain embodiments, the at least one recombinant modified haemoglobin chain subunit comprises the at least one further modification. By way of example the at least one recombinant modified haemoglobin chain subunit may comprise one, two three, four, five, six or more additional amino acid residue substitutions, deletions and/or insertions (which may be contiguous or non-contiguous). These further modifications may affect further properties of the modified protein such as assembly rate, porphyrin loss, metallic ion autoxidation rate, resistance to proteolytic degradation, aggregation, nitric oxide reactivity and nitric oxide binding, production and purification means and solubility. Such modifications will be known by those skilled in the art and may be incorporated into the conjugates of embodiments of the present invention.

In certain embodiments, the at least one further modification comprises one or more of:
a. one or more modifications for decreasing a nitric oxide reactivity;
b. one or more modifications for introducing or enhancing reduction of at least one metallic ion associated with the at least one recombinant modified haemoglobin chain subunit thereby increasing the rate at which an oxidised form of the conjugate is capable of re-oxygenation to an oxygen-binding form; and/or
c. one or more modifications for improving production and/or purification of the at least one recombinant modified haemoglobin chain subunit.

By way of example, modifications for introducing or enhancing reduction of at least one metallic ion associated with the at least one recombinant modified haemoglobin chain subunit thereby increasing the rate at which an oxidised form of the conjugate is capable of re-oxygenation to an oxygen-binding form, wherein the at least one recombinant modified haemoglobin chain subunit is an alpha chain subunit may include but are not limited αL29F and/or αL91Y.

Without being bound by theory, in certain embodiments the at least one further modification introduces or enhances an electron transfer pathway to the at least one metallic ion associated with the at least one recombinant modified haemoglobin chain subunit via at least one redox-active amino acid residue introduced into the haemoglobin chain subunit by the at least one further modification. This electron transfer pathway via the redox-active amino acid residue may have a higher affinity than a direct electron transfer pathway to the at least one metallic ion and so can result in more rapid reduction of the at least one metallic ion.

By way of example, modifications for improving production and/or purification of the at least one recombinant modified haemoglobin chain subunit may include but are not limited to a substitution of the most N-terminal amino acid residue with a methionine residue. For example, wherein the at least one recombinant modified haemoglobin chain subunit is an alpha chain subunit the at least one further modification may include but is not limited to αV1M. It will be understood by those skilled in the art that if the haemoglobin chain subunit includes the methionine encoded by the start codon that is cleaved from the mature protein then deletion of V1, also referred to as V1Del (V2 in the precursor protein) would provide the same final amino acid residue sequence as the mutation of V1M.

In certain embodiments, wherein the at least one recombinant modified haemoglobin chain subunit comprises a haemoglobin alpha chain subunit, the at least one further modification is selected from one or more of: αV1M, αL29F and/or αL91Y or a combination thereof.

In certain embodiments, the at least one recombinant modified haemoglobin chain subunit comprises a plurality of further modifications.

In certain embodiments, when the at least one recombinant modified haemoglobin chain subunit comprises a haemoglobin alpha chain subunit, the haemoglobin alpha chain subunit comprises the at least one modification αA19C and the further modifications αV1M and αL29F.

In certain embodiments, when the at least one recombinant modified haemoglobin chain subunit comprises a haemoglobin alpha chain subunit, the haemoglobin alpha chain subunit comprises the at least one modification αA19C and the further modifications αV1M and αL91Y.

In certain embodiments, when the at least one recombinant modified haemoglobin chain subunit comprises a haemoglobin alpha chain subunit, the haemoglobin alpha chain subunit comprises the at least one modification αA19C and the further modifications αV1M, αL29F and αL91Y.

In certain embodiments, when the at least one recombinant modified haemoglobin chain subunit comprises a haemoglobin beta chain subunit, endogenous amino acid residue 13 does not comprise a reactive thiol group. Aptly, the amino acid residue 13 comprises the endogenous corresponding wild-type amino acid residue at this position (e.g. alanine (A)).

In certain embodiments, the conjugate comprises at least one recombinant modified haemoglobin chain subunit comprising or consisting of an amino acid sequence with at least 80% e.g. 85%, e.g. 90%, e.g. 95, 96, 97, 98 or 99% sequence identity to an amino acid sequence as set forth in SEQ. ID. NO. 5.

In certain embodiments, the conjugate comprises at least one recombinant modified haemoglobin chain subunit comprising or consisting of an amino acid sequence with at least 80% e.g. 85%, e.g. 90%, e.g. 95, 96, 97, 98 or 99% sequence identity to an amino acid sequence as set forth in SEQ. ID. NO. 6.

In certain embodiments, the conjugate comprises at least one recombinant modified haemoglobin chain subunit comprising or consisting of an amino acid sequence with at least 80% e.g. 85%, e.g. 90%, e.g. 95, 96, 97, 98 or 99% sequence identity to an amino acid sequence as set forth in SEQ. ID. NO. 7.

Multimers

In certain embodiments, the conjugate is a multimer protein. In certain embodiments, the conjugate is a dimer. In certain embodiments, the conjugate is a trimer. In certain embodiments, the conjugate is a tetramer.

According to a further aspect of the present invention there is provided a recombinant modified multimeric protein comprising;
a. a conjugate protein comprising;
i. at least one polymeric moiety; and
ii. at least one recombinant modified haemoglobin chain subunit;
wherein the at least one recombinant modified haemoglobin chain subunit comprises at least one modification for introducing at least one exogenous amino acid residue to the at least one haemoglobin chain subunit for conjugation to the at least one polymeric moiety; and wherein the at least one polymeric moiety is conjugated to the at least one exogenous amino acid residue; and
further wherein the conjugate has at least one unaltered or improved property selected from: at least one oxygen binding property; a rate of oxidation and/or reduction of a haem molecule of the haemoglobin chain subunit; and/or a stability of the haemoglobin chain subunit as compared to a reference protein, wherein said reference protein is a protein comprising the recombinant modified haemoglobin chain subunit without the at least one polymeric moiety; and
b. at least one further haemoglobin chain subunit.

Aptly, the at least one conjugate is a conjugate as described herein.

In certain embodiments, the at least one further haemoglobin chain subunit comprises at least one alpha chain subunit.

In certain embodiments, the at least one further haemoglobin chain subunit comprises at least one beta chain subunit.

In certain embodiments, the at least one further haemoglobin chain subunit comprises at least one gamma chain subunit.

In certain embodiments, the at least one further haemoglobin chain subunit comprises at least one delta chain subunit.

Aptly the at least one further haemoglobin chain subunit is a mammalian haemoglobin chain subunit. Aptly the at least one further haemoglobin chain subunit is a human haemoglobin chain subunit.

In certain embodiments, the at least one further haemoglobin chain subunit comprises one or more modifications and/or further modifications as described herein.

In certain embodiments, the at least one further haemoglobin chain subunit comprises one or more modifications for preventing conjugation with the at least one polymeric moiety. Such modifications may involve the substitution and/or deletion of amino acid residues comprising a reactive thiol group e.g. cysteines that are located at a position on the multimer when assembled in a secondary, tertiary and/or quaternary structure, that is solute accessible and so therefore may contact and react with a polymeric moiety as described herein and undergo a conjugation reaction. By removing reactive thiol groups, the reactive partner and/or site of conjugation for polymeric moieties as described herein are no longer available therefore preventing conjugation to a polymeric moiety as described herein. Reactive thiol groups that may be able to undergo conjugation reactions may be determined using methods such as but not limited to, analysing the three-dimensional structure of a protein using x-ray crystallography methods and/or nuclear magnetic resonance methods, other methods will be known by those skilled in the art.

In certain embodiments, wherein the at least one further haemoglobin chain subunit is a haemoglobin beta or gamma chain subunit the one or more modifications for preventing conjugation with the at least one polymeric moiety may be the deletion and/or substitution of the amino acid residue cysteine 93 (C93) (i.e. βC93 or γC93). Without being bound by theory the amino acid residue C93 comprises a reactive thiol group which may undergo conjugation to a polymeric moiety. Conjugation of a polymeric moiety to C93 may cause disruption of dimerization of haemoglobin chain subunits and therefore reduce stability of a haemoglobin multimer as well alter the oxygen binding properties of a haemoglobin chain subunit by interacting with the haem molecule bound by the haemoglobin chain subunit.

In certain embodiments, the modification for preventing conjugation with the at least one polymeric moiety is the substitution of the amino acid residue C93 with an amino acid residue which does not comprise a reactive thiol group.

In certain embodiments, the one or more modifications for preventing conjugation with the at least one polymeric moiety is the substitution C93A. It will be understood by those skilled in the art that a number of different amino acid residues may be used as the substituent for C93 for example, glycine, valine or leucine.

Thus, in certain embodiments, the one or more modifications may be selected from one or more of:
a. one or more modifications for decreasing a nitric oxide reactivity;
b. one or more modifications for introducing or enhancing reduction of at least one metallic ion associated with the at least one further haemoglobin chain subunit thereby increasing a rate at which an oxidised form of the modified oxygen-carrying conjugate is capable of re-oxygenation to an oxygen-binding form;
c. one or more modifications for improving production and/or purification of the at least one further haemoglobin chain subunit; and/or
d. one or more modifications for preventing conjugation with the at least one polymeric moiety.

In certain embodiments, when the at least one further haemoglobin chain subunit is a haemoglobin beta chain subunit the one or more modifications may be selected from one or more of: βC93A, βV1M (also referred to as βV1 Del), βV67F and/or βL96Y or a combination thereof.

In certain embodiments, when the at least one further haemoglobin chain subunit is a haemoglobin gamma 1 or gamma 2 chain subunit the one or more modifications may be selected from one or more of: γC93A, γG1M (also referred to as γG1 Del), γL96Y and/or γV67F or a combination thereof.

In certain embodiments, the at least one further haemoglobin chain subunit is non-conjugated.

In certain embodiments, the recombinant modified multimeric protein comprises at least one conjugate, wherein the at least one conjugate comprises at least one haemoglobin alpha chain subunit, and wherein the at least one haemoglobin alpha chain subunit comprises the at least one modification αA19C; and further comprises at least one further haemoglobin chain subunit, wherein the at least one further haemoglobin chain subunit comprises at least one haemoglobin beta chain subunit, and wherein the at least one beta chain subunit comprises the modification βC93A.

In certain embodiments, the recombinant modified multimeric protein, comprises at least one conjugate, wherein the at least one conjugate comprises at least one haemoglobin alpha chain subunit, and wherein the at least one haemoglobin alpha chain subunit comprises the at least one modification αA19C and the further modifications αV1M and αL29F; and further comprises at least one further haemoglobin chain subunit wherein the at least one further haemoglobin chain subunit comprises at least one haemoglobin beta chain subunit, and wherein the at least one beta chain subunit comprises the modifications βC93A, βV1M, βV67F and βT84Y.

In certain embodiments, the recombinant modified multimeric protein comprises at least one conjugate, wherein the at least one conjugate comprises at least one haemoglobin alpha chain subunit, and wherein the at least one haemoglobin alpha chain subunit comprises the at least one modification αA19C; and further comprises at least one further haemoglobin chain subunit, and wherein the at least one further haemoglobin chain subunit comprises at least one haemoglobin gamma chain subunit, and wherein the at least one haemoglobin gamma chain subunit comprises the modification γC93A.

In certain embodiments, the recombinant modified multimeric protein comprises:
at least one conjugate, wherein the at least one conjugate comprises at least one haemoglobin alpha chain subunit, and wherein the at least one haemoglobin alpha chain subunit comprises the at least one modification αA19C and the further modifications αV1M and αL29F; and further comprises at least one further haemoglobin chain subunit, wherein the at least one further haemoglobin chain subunit comprises at least one haemoglobin gamma chain subunit, and wherein the at least one haemoglobin gamma chain subunit comprises the modifications γC93A, γG1M, γV67F and γT84Y.

In certain embodiments, the recombinant modified multimeric protein comprises at least one conjugate, wherein the at least one conjugate comprises at least one recombinant modified haemoglobin chain subunit comprising an amino acid sequence having at least about 80% e.g. 85%, 90%, e.g. 95, 96, 97, 98 or 99% sequence identity to a sequence selected from one or more of:
  a. SEQ ID NO: 5;
  b. SEQ ID NO: 6; and/or
  c. SEQ ID NO: 7
  and wherein, the recombinant modified multimeric protein further comprises at least one further haemoglobin chain subunit comprising an amino acid sequence having at least about 80% e.g. 85%, e.g. 90%, e.g. 95, 96, 97, 98 or 99% sequence identity to a sequence selected from one or more of:
  d. SEQ ID NO: 8
  e. SEQ ID NO: 9
  f. SEQ ID NO: 10;
  g. SEQ ID NO: 11;
  h. SEQ ID NO: 12;
  i. SEQ ID NO: 13;
  j. SEQ ID NO: 14;
  k. SEQ ID NO: 15;
  l. SEQ ID NO: 16;
  m. SEQ ID NO: 17; and/or
  n. SEQ ID NO: 18.

In certain embodiments, the recombinant modified multimeric protein is a haemoglobin. In certain embodiments, the haemoglobin is an adult haemoglobin. Aptly, a human adult haemoglobin. In certain embodiments, the haemoglobin is a foetal haemoglobin. Aptly, a human foetal haemoglobin. Non-limiting examples of naturally occurring human haemoglobins are given in Table 1. The most common form of haemoglobin found in humans is $\alpha_2\beta_{32}$ (also referred to as adult haemoglobin) i.e. it is composed of two alpha chain subunits and two beta chain subunits. An example of foetal haemoglobin is $\alpha_2\gamma_2$ (i.e. it is composed of two alpha chain subunits and two gamma chain subunits).

TABLE 1

Types of human haemoglobins

| Name | Subunits |
| --- | --- |
| Gower 1 | $\zeta_2\epsilon_2$ |
| Gower 2 | $\alpha_2\epsilon_2$ |
| Haemoglobin Portland I | $\zeta_2\gamma 1_2$ or $\zeta_2\gamma 2_2$ |
| Haemoglobin Portland II | $\zeta_2\beta_2$ |
| Haemoglobin F | $\alpha_2\gamma 1_2$ or $\alpha_2\gamma 2_2$ |
| Haemoglobin A | $\alpha_2\beta_2$ |
| Haemoglobin A$_2$ | $\alpha_2\delta_2$ |
| Haemoglobin H | $\beta_4$ |
| Haemoglobin Barts | $\gamma_4$ |

In certain embodiments, the recombinant modified multimeric protein is a haemoglobin comprising a first conjugate as described herein, and second conjugate as described herein and further comprises a first further haemoglobin chain subunit as described herein, and a second further haemoglobin chain subunit as described herein.

In certain embodiments, the recombinant modified multimeric protein is a human adult haemoglobin.

In certain embodiments, the recombinant modified multimeric protein comprises:

a first conjugate as described herein, wherein the at least one recombinant haemoglobin chain subunit is a first haemoglobin alpha chain subunit, and wherein the first haemoglobin alpha chain subunit comprises the at least one modification αA19C;

a second conjugate as described herein, wherein the at least one recombinant haemoglobin chain subunit is a second haemoglobin alpha chain subunit, and wherein the second haemoglobin alpha chain subunit comprises the at least one modification αA19C;

a first further haemoglobin chain subunit, wherein the first further haemoglobin chain subunit is a first haemoglobin beta chain subunit, and wherein the first haemoglobin beta chain subunit comprises the modification βC93A; and a second further haemoglobin chain subunit, wherein the second further haemoglobin chain subunit is a second haemoglobin beta chain subunit, and wherein the second haemoglobin beta chain subunit comprises the modification βC93A.

In certain embodiments, the haemoglobin alpha chain subunits of the first and second conjugate each independently further comprise at least one further modification as described herein. In certain embodiments, the first and second haemoglobin alpha chain subunits of the first and second conjugate each independently further comprise one or more further modifications selected from: αV1M, αL29F and/or αL91Y or a combination thereof.

In certain embodiments, the first and second haemoglobin beta chain subunits each independently further comprise one or more modifications selected from: βV1M, βV67F, βT84Y, βF85Y and/or βL96Y or a combination thereof.

In an alternative embodiment, the recombinant modified multimeric protein is a human foetal haemoglobin.

In certain embodiments, the recombinant modified multimeric protein comprises:

a first conjugate as described herein, wherein the at least one recombinant haemoglobin chain subunit is a first haemoglobin alpha chain subunit, and wherein the first haemoglobin alpha chain subunit comprises the at least one modification αA19C;

a second conjugate as described herein, wherein the at least one recombinant haemoglobin chain subunit is a second haemoglobin alpha chain subunit, and wherein the second haemoglobin alpha chain subunit comprises the at least one modification αA19C;

a first further haemoglobin chain subunit, wherein the first further haemoglobin chain subunit is a first haemoglobin gamma chain subunit, and wherein the first haemoglobin gamma chain subunit comprises the modification γC93A; and a second further haemoglobin chain subunit, wherein the second further haemoglobin chain subunit is a second haemoglobin gamma chain subunit, and wherein the second haemoglobin gamma chain subunit comprises the modification γC93A.

In certain embodiments, the first and second haemoglobin alpha chain subunits of the first and second conjugate each independently further comprise at least one further modification as described herein. In certain embodiments, the haemoglobin alpha chain subunits of the first and second conjugate each independently further comprise one or more further modifications selected from: αV1M, αL29F and/or αL91Y.

In certain embodiments, the first and second haemoglobin gamma chain subunits each independently further comprise one or more modifications selected from: γG1M, γV67F, γT84Y, γF85Y and/or γL96Y.

In certain embodiments, the first and second haemoglobin gamma chain subunits are haemoglobin gamma 1 chain subunits. In certain embodiments, the first and second haemoglobin gamma chain subunits are haemoglobin gamma 2 chain subunits.

In certain embodiments, the recombinant modified multimeric protein is cross linked. Methods of cross linking proteins will be known by those skilled in the art but by way of example suitable cross-linking methods may include but are not limited to chemical cross lining and fusion protein recombinant expression.

Nucleic Acids

In one aspect of the present invention there is provided a nucleic acid sequence encoding a recombinant modified haemoglobin chain subunit and/or further haemoglobin chain subunit of the present invention.

In certain embodiments, the nucleic acid sequence may be DNA or RNA. In certain embodiments, the sequence may be double stranded DNA. In certain embodiments, the sequence may be single stranded DNA.

In certain embodiments, the nucleic acid sequence is isolated and/or purified. In certain embodiments, the nucleic acid sequence is substantially free or free from material which it may be associated with.

In certain embodiments, the nucleic acid sequence of the present invention may be obtained by modification of a wild-type nucleic acid encoding a haemoglobin chain subunit. The nucleic acid sequences encoding for carrying a haemoglobin chain subunit will be known by those skilled in the art.

In certain embodiments, recombinant DNA techniques such as site directed mutagenesis may be used to modify a nucleic acid sequence such that the nucleic acid sequence encodes for a recombinant modified haemoglobin chain subunit and/or further haemoglobin chain subunit of the present invention. Other suitable methods will be known by those skilled in the art.

In certain embodiments, the nucleic acid sequence of the present invention may be incorporated into a recombinant replicable vector. In certain embodiments, the vector is used to replicate the nucleic acid in a compatible host cell.

Thus, in a further aspect of the present invention there is provided a method of producing recombinant modified haemoglobin chain subunit and/or further haemoglobin chain subunit as described herein comprising the steps of introducing a nucleic acid encoding the modified protein into a replicable vector, introducing the vector into a compatible host cell and culturing the host cell under conditions to bring about the replication of the vector.

In a further aspect of the present invention there is provided a method of producing a recombinant modified haemoglobin chain subunit and/or further haemoglobin chain subunit of the present invention comprising the steps of:
  transfecting a host cell with a nucleic acid of the present invention;
  inducing the host cell to express the recombinant modified haemoglobin chain subunit and/or further haemoglobin chain subunit of the present invention; and
  isolating the recombinant modified haemoglobin chain subunit and/or further haemoglobin chain subunit of the present invention.

In certain embodiments, the method further comprises a step of purifying the isolated recombinant modified haemoglobin chain subunit and/or further haemoglobin chain subunit of the present invention.

Reference Proteins

In certain embodiments, the reference protein comprises at least one of an unconjugated form of a recombinant modified haemoglobin chain subunit as described herein. In certain embodiments, the reference protein has an identical sequence to the haemoglobin chain subunit protein of the conjugate.

In certain embodiments, the reference protein comprises at least one unconjugated recombinant modified haemoglobin chain subunit comprising or consisting of an amino acid sequence with at least 80% e.g. 85%, e.g. 90%, e.g. 95, 96, 97, 98, 99% or 100% sequence identity to an amino acid sequence as set forth in one or more of SEQ. ID. NO. 5, SEQ. ID. NO. 6 and/or SEQ. ID. NO.7.

"Percent (%) amino acid sequence identity" as used herein is defined as the percentage of amino acid residues in a candidate sequence that are identical with the amino acid residues in a specific modified oxygen-carrying protein, after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN or ClustalW software. Those skilled in the art can determine appropriate parameters for measuring alignment, including any algorithms needed to achieve maximal alignment over the full length of the sequences being compared.

In certain embodiments, the reference protein is an unconjugated form of a recombinant modified multimeric protein as described herein.

In certain embodiments, the reference protein is an unconjugated recombinant modified multimeric protein comprising at least one recombinant modified haemoglobin chain subunit, wherein the haemoglobin chain subunit comprises an amino acid sequence having at least about 80% e.g. 85%, 90%, e.g. 95, 96, 97, 98, 99% or 100% sequence identity to a sequence selected from one or more of:
  a. SEQ ID NO: 5;
  b. SEQ ID NO: 6; and/or
  c. SEQ ID NO: 7
  and wherein the reference protein further comprises, at least one further haemoglobin chain subunit, wherein the further haemoglobin chain subunit comprises an amino acid sequence having at least about 80% e.g. 85%, e.g. 90%, e.g. 95, 96, 97, 98, 99% or 100% sequence identity to a sequence selected from one or more of:
  d. SEQ ID NO: 8
  e. SEQ ID NO: 9
  f. SEQ ID NO: 10;
  g. SEQ ID NO: 11;
  h. SEQ ID NO: 12;
  i. SEQ ID NO: 13;
  j. SEQ ID NO: 14;
  k. SEQ ID NO: 15;
  l. SEQ ID NO: 16; and/or m. SEQ ID NO: 17.

In certain embodiments, the reference protein is an unconjugated recombinant modified multimeric protein, comprising at least one unconjugated haemoglobin alpha chain subunit comprising the at least one modification αA19C; and wherein the reference protein further comprises at least one unconjugated haemoglobin beta chain subunit comprising the modification βC93A (or substitution with any amino acid other than A which does not comprise a reactive thiol group).

In certain embodiments, the reference protein is an unconjugated recombinant modified multimeric protein, comprising at least one unconjugated haemoglobin alpha chain subunit comprising the modifications αA19C, αV1M and αL29F; and wherein the reference protein further comprises, at least one unconjugated haemoglobin beta chain subunit, comprising the modifications βC93A, βV1M, βV67F and βT84Y.

In certain embodiments, the reference protein is an unconjugated recombinant modified multimeric protein, comprising at least one unconjugated haemoglobin alpha chain subunit comprising the at least one modification αA19C; and wherein the reference protein further comprises, at least one unconjugated haemoglobin gamma chain subunit, comprising the modification γC93A.

In certain embodiments, the reference protein is an unconjugated recombinant modified multimeric protein, comprising at least one unconjugated haemoglobin alpha chain subunit comprising the modifications αA19C, αV1M and αL29F; and wherein the reference protein further comprises, at least one unconjugated haemoglobin gamma chain subunit, comprising the modifications γC93A, γG1M, γV67F and γT84Y.

In certain embodiments, the "reference protein" is a native and/or recombinant wild-type protein as described herein. That is to say, the reference protein may be the wild-type version of the unconjugated haemoglobin chain subunit. Alternatively, the reference protein may comprise one or more further modifications as described herein compared to the wild-type protein.

For example, the reference protein may contain at least 1, 2, 3, 4, 5, 6, 7, 8, 9, 10 or more amino acid substitutions, deletions or insertions as compared to a wild-type oxygen-carrying polypeptide sequence.

Substitutions may be naturally occurring or non-naturally occurring. In certain embodiments, the reference protein may comprise a modification which substitutes the first (N-terminal) amino acid residue substituted with a methionine. For example, the reference protein may be a human haemoglobin beta chain subunit in which the first amino acid residue (valine) of a wild-type human haemoglobin beta chain subunit has been substituted with a methionine as set forth in SEQ. ID. No. 14 (also referred to as βV1M).

In certain embodiments, the reference protein may be a human haemoglobin alpha chain subunit wherein the first amino acid residue (valine) of a wild-type human haemoglobin alpha chain subunit has been substituted with a methionine as set forth in SEQ. ID. No. 15 (also referred to as αV1M).

In certain embodiments, the reference protein may be a human haemoglobin gamma 1 chain subunit in which the first amino acid residue (glycine) of the wild-type human haemoglobin gamma 1 chain subunit has been substituted with a methionine as set forth in SEQ. ID. No. 16 (also referred to as γ1G1M).

In certain embodiments, the reference protein may be a human haemoglobin gamma 2 chain subunit in which the first amino acid residue (glycine) of the wild-type human haemoglobin gamma 2 chain subunit has been substituted with a methionine as set forth in SEQ. ID. No. 17 (also referred to as γ2G1M).

The modifications described above may help with recombinant expression, purification and/or isolation of a protein.

Properties

Certain embodiments of the present invention may have unaltered or improved properties such as at least one oxygen binding property, a rate of oxidation and/or reduction of a haem molecule and/or stability as compared to a reference protein as described herein.

In certain embodiments, the at least one oxygen binding property comprises a Hill coefficient of the conjugate.

As used herein, the term "Hill's coefficient" describes the fraction of a macromolecule, such as a protein, saturated by a ligand as a function of the ligand concentration; it is used in determining the degree of cooperativeness of the ligand binding to the macromolecule. As used herein, the term "cooperativity" in reference to ligand binding to a macromolecule, refers to enhanced ligand binding when there are already other ligands present on the same macromolecule. Hill's coefficient may be determined using the Hill's equation which is described in Magnus, Wilhelm, and Stanley Winkler. Hill's equation. Courier Corporation, 2013 which is incorporated herein by reference.

Figure 7:
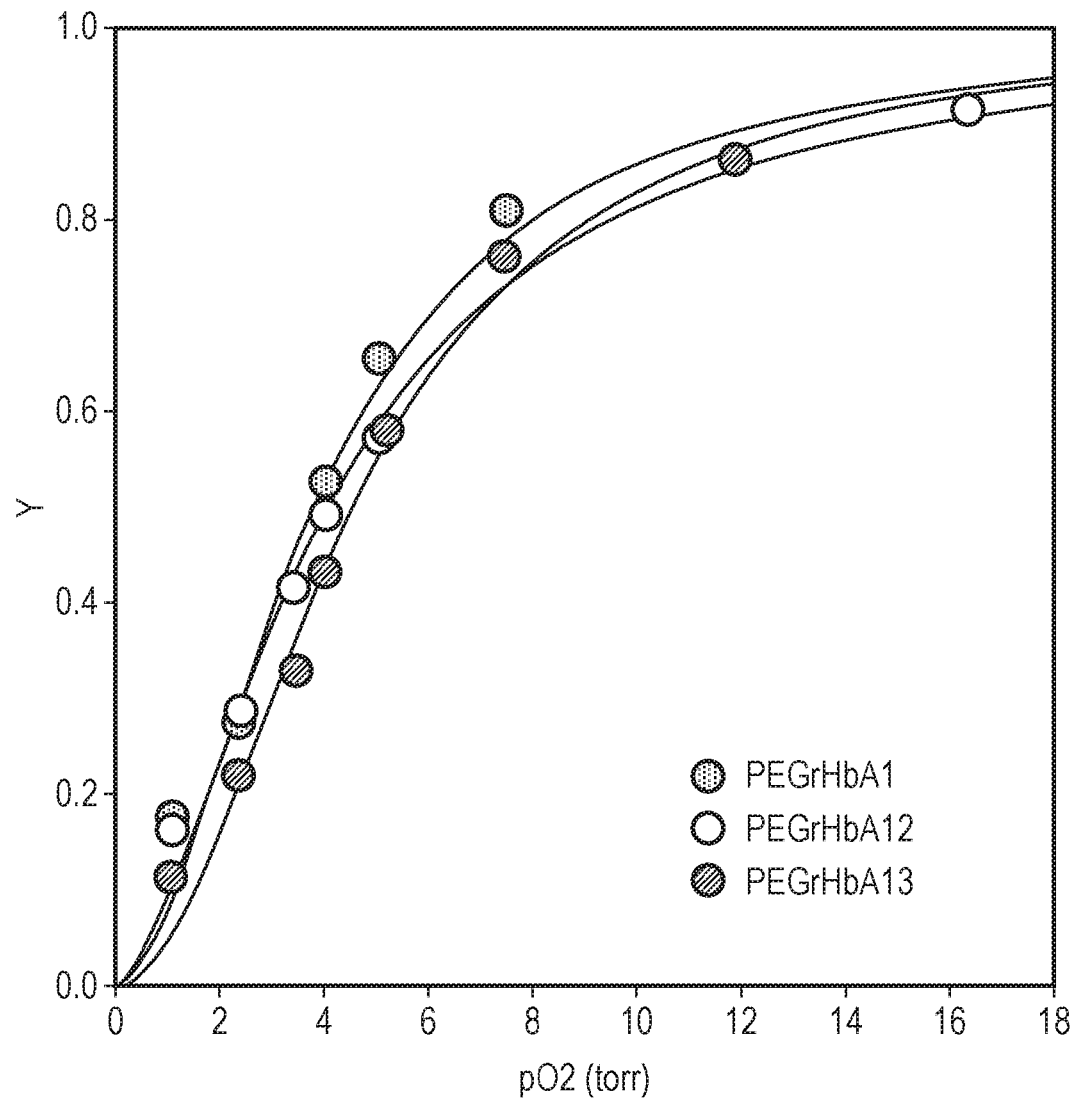
FIG. 7 shows a graph showing the fraction of haemoglobin in an oxygenated state at different partial pressures of oxygen ($pO_2$) (referred to as an oxygen binding curve) for PEGylated A1, PEGylated A12 and PEGylated A13. PEGylation of wild type haemoglobin (A1) lowers oxygen affinity but PEGylation at A12 and A13 has no effect on either oxygen affinity (p50) or the co-operativity of oxygen binding (Hill coefficient). See also Table 2. p50 measurements was carried out in 100 mM HEPES, 100 mM sodium chloride, 1.2 mM sodium phosphate, 1 mM EDTA, pH 7.0. The final protein concentration was 100 μM (determined from the concentration of haem)

Hill's coefficient can be determined by obtaining a plot of haemoglobin saturation against partial pressure of oxygen, also referred to as an oxygen dissociation curve, (for example see FIG. 7) for a protein of interest. Oxygen-haemoglobin dissociation curves represents the affinity of haemoglobin for oxygen. The p50 value represents a mid-point in this curve, and can provide information regarding the affinity of oxygen for the haemoglobin.

As used herein, the term "partial pressure" refers the hypothetical pressure of a gas if the gas alone occupied the entire volume of the original mixture at the same temperature. Such a plot may be obtained using any known methods in the art (see for example Ronda et al., Methods in Enzymology 437, 311-328, Natelson, Samuel. Principles of Applied Clinical Chemistry: Chemical Background and Medical Applications. Volume 3: Plasma Proteins in Nutrition and Transport. Springer Science & Business Media, 2012 and Samaja, Michele, and Ermanna Rovida. Journal of biochemical and biophysical methods 7.2 (1983): 143-152).

In certain embodiments, the modification is capable of a change (e.g. increase or decrease) in oxygen affinity of no more than about 5% or less, no more than about 4% or no more than about 3% or less of the conjugate as compared to a reference protein as described herein. For example, the reference protein may be a corresponding unconjugated recombinant modified multimeric protein (e.g. as measured under substantially the same conditions). See, for example, FIG. 7 and Table 2.

In certain embodiments, the rate of oxidation and/or reduction of a haem molecule of the recombinant modified haemoglobin chain subunit is a rate of autoxidation of the haem group of the at least one recombinant modified haemoglobin chain subunit.

In certain embodiments, the rate of autoxidation is the rate of oxidation of oxy-haemoglobin (ferrous ($Fe^{2+}$) haemoglobin) to met-haemoglobin (ferric ($Fe^{3+}$) haemoglobin).

Figure 6A:
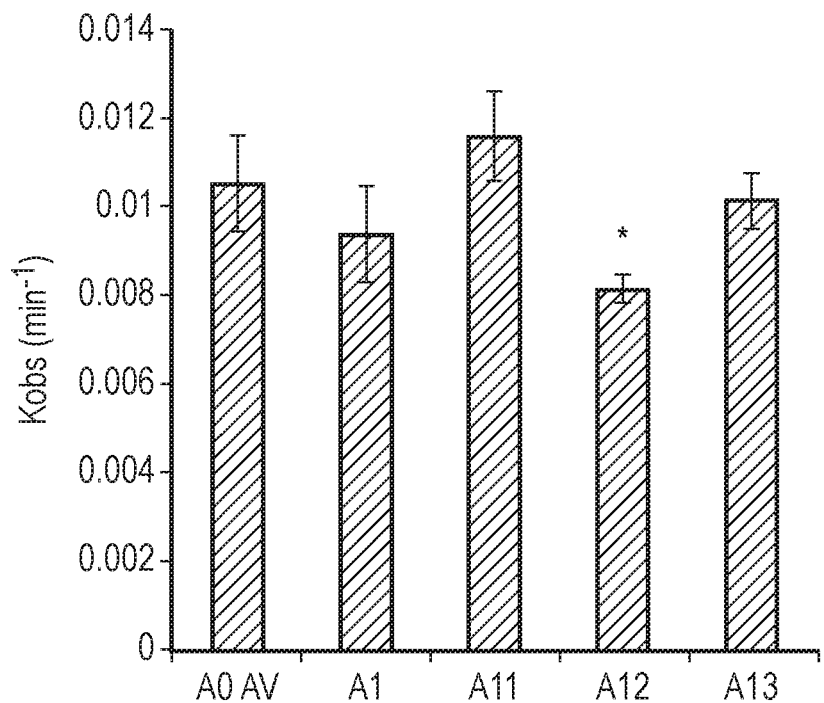
FIG. 6 shows comparison of autoxidation rate (6A) and haem release (6B) for un-conjugated mutants A12 and A13 compared to un-conjugated controls A0 (Native WT), A1 (recombinant WT) and A11. It is noted that A12 has a lower autoxidation rate and decreased haem loss compared to native haemoglobin confirming that the introduction of the new reactive thiol group (—SH group) introduced by the modification αA19C has not destabilised the protein. Autoxidation: 10 μM oxyHb was incubated at 37° C. in 70 mM sodium phosphate buffer, pH 7.2. Time courses (406-500 nm) were fitted to a single exponential function (n=3). Statistical significance was determined using a student's t-test to compare each rHb to native Hb (A0)*p<0.005. Haem Release: 3 μM metHb was incubated with 30 μM apo SW Mb (H64Y/V67F) in 0.15M sodium acetate, 0.4M sucrose, pH 5 at 37° C. The time courses (600-650 nm) were fitted to a single exponential function (n=6). Statistical significance was determined using the students t-test to compare each rHb to native Hb (A0) **p<0.001, *p<0.05, #p<0.0075.

In certain embodiments, the modification is capable of an increase in the rate of autoxidation of no more than about 5% or less, no more than about 4% or less or no more than about 3% or less of the conjugate as compared to a reference protein as described herein. For example, the reference protein may be a corresponding wild-type protein (e.g. as measured under substantially the same conditions). See, for example, FIG. 6A. Alternatively, the reference protein may be a corresponding unconjugated recombinant modified multimeric protein (e.g. as measured under substantially the same conditions). See, for example, FIG. 8B.

Aptly, the at least one modification is capable of a decrease in the rate of autoxidation of about 5%, 10%, 15%, 20%, 25%, 30%, 35% or more of the conjugate as compared to a reference protein as described herein. For example, the reference protein may be a corresponding unconjugated recombinant modified multimeric protein (e.g. as measured under substantially the same conditions). See, for example, FIG. 8B.

In certain embodiments, the at least one oxygen binding property comprises a partial pressure of a gas required to achieve 50% saturation (also referred to as p50) of the conjugate.

In certain embodiments, the stability of the at least one recombinant modified haemoglobin chain subunit is measured by a rate of release of the haem molecule from the at least one recombinant modified haemoglobin chain subunit.

Measurements of haem release can be carried out using methods described herein in the examples. One non-limiting example of a method includes: measuring the absorbance changes with a heme acceptor, such as a double-mutant myoglobin (Mb) comprising the mutations H64Y/V68F or hemopexin (Hpx). His 64(E7) is replaced by Tyr in sperm whale Mb producing a holoprotein with distinct green colour due to an intense absorption band at 600 nm. Val 68(E11) may be replaced by phenylalanine in the same protein to increase its stability. When this double-mutant apoglobin is mixed with either metMb or metHb, a colorimetric change occurs (the brown solution turns green); the resulting absorbance changes can be used to measure complete time courses for haem dissociation from either holoMb or holoHb. Other methods will be known by those skilled in the art (see for example Kassa T, Jana S, Meng F, Alayash Al. FEBS Open Bio. 2016; 6(9):876-884. doi:10.1002/2211-5463.12103 and Aich A, Freundlich M, Vekilov P G. Blood cells, molecules & diseases. 2015; 55(4):402-409. doi: 10.1016/j.bcmd.2015.09.003.)

Figure 6B:
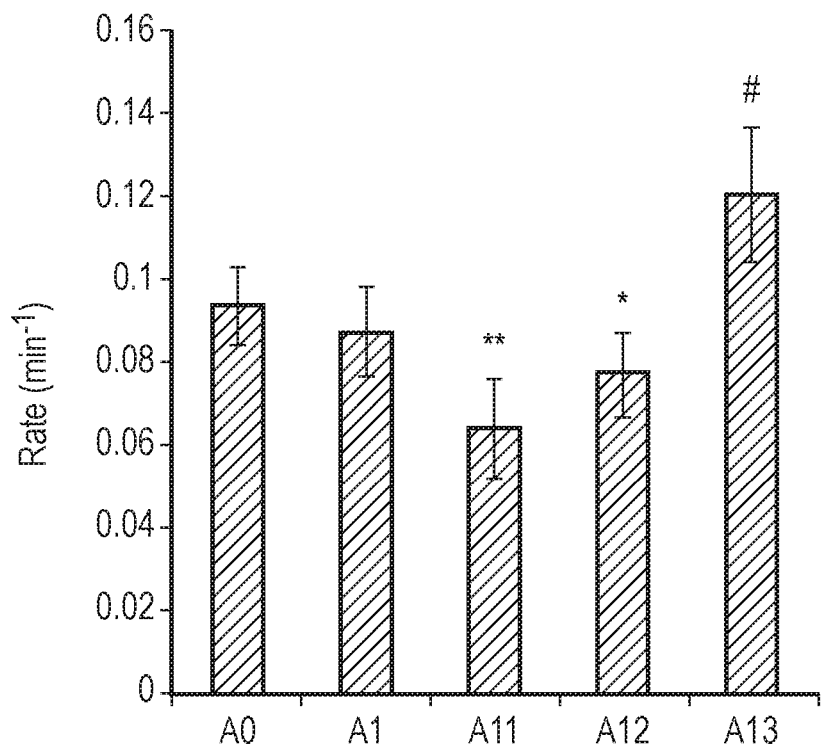

In certain embodiments, the modification is capable of an increase in the rate of haem loss of no more than about 5% or less, no more than about 4% or less or no more than about 3% or less of the conjugate as compared to a reference protein as described herein. For example, the reference protein may be a corresponding wild-type protein (e.g. as measured under substantially the same conditions). See, for example, FIG. 6B. Alternatively, the reference protein may be a corresponding unconjugated recombinant modified multimeric protein (e.g. as measured under substantially the same conditions). See, for example, FIG. 8A.

Aptly, the at least one modification is capable of a decrease in the rate of haem loss of about 1%, 2%, 3%, 4%, 5%, 6%, 7%, 8% or more of the conjugate as compared to a reference protein as described herein. For example, the reference protein may be a corresponding unconjugated recombinant modified multimeric protein (e.g. as measured under substantially the same conditions). See, for example, FIG. 8A.

Polymeric Moieties

The conjugate described herein comprises at least one polymeric moiety. In certain embodiments, the polymeric moiety is water-soluble, non-toxic and pharmaceutically inert.

In certain embodiments, the at least one polymeric moiety is a non-naturally occurring polymeric moiety. As used herein "non-naturally occurring" with respect to a polymeric moiety, refers to a polymeric moiety that in its entirety is not found in nature. A non-naturally occurring polymeric moiety may, however, contain one or more monomers or segments of monomers that are naturally occurring, so long as the overall polymer structure is not found in nature.

In certain embodiments, the polymeric moiety comprises a thiol-selective functional group. As used herein "thiol-selective functional group" refers to a polymeric moiety having at least one terminus that comprises chemical group that reacts preferentially with reactive thiol groups (for example, thiol groups of cysteine amino acid residues) in order to form a chemical bond and therefore conjugate the polymeric moiety to a target via the reactive thiol group.

By way of example, thiol-selective functional groups include but are not limited to maleimide, vinyl sulfone, orthopyridyl disulfide, iodoacetamide, thiol or thiolate. Examples of suitable thiol-selective polymeric moieties and methods for their production can be found in International patent application WO2004063250A1 which is incorporated herein by reference.

In certain embodiments, the at least one polymeric moiety is conjugated to at least one exogenous amino acid residue as described herein via a thiol-selective group selected from:

a. at least one maleimide group;
b. at least one vinylsulfone group;
c. at least one thiol group; and/or
d. at least one orthopyridyl disulphide group.

In certain embodiments, the polymeric moiety comprises at least one polyalkylene glycol (PAG) or derivatives thereof. In certain embodiments, the polymeric moiety comprises at least one polyethylene glycol (PEG) or derivatives thereof.

The polymeric moiety used can be of any molecular weight, and can be branched or unbranched. In certain embodiments, the polyalkylene glycol has a molecular weight between about 1000 Daltons and about 100,000 Da (the term "about" indicating that in preparations of polyalkylene glycols, some molecules will weigh more, some less, than the stated molecular weight). For example, the polyalkylene glycol can have an average molecular weight of about 1000, 5000, 10000, 15000, 20000, 25000, 30000, 35000, 40000, 50000, 60000, 70000, 80000, 90000 or 100000 Da.

In certain embodiments, the polymeric moiety has a molecular weight of about 20,000 kDa.

Aptly, the polymer moiety is a thiol-selective polyethylene glycol derivative and in some embodiments, the at least one recombinant modified haemoglobin chain subunit as described herein is "pegylated". As used herein, the terms "pegylated" and "pegylation" have their general meaning in the art and refer generally, for example, to the process of chemically modifying a haemoglobin chain subunit as described herein by covalent attachment of one or more molecules of polyethylene glycol or a derivative thereof, such as by reacting a thiol-selective polyalkylene glycol, with a free thiol group or free thiol group containing moiety such as an amino acid, e.g. cysteine, to form a covalent bond.

Aptly, the polymeric moiety is a maleimide functionalised polyethylene glycol.

In certain embodiments, the at least one recombinant modified haemoglobin chain subunit is further conjugated to at least one protecting group.

In certain embodiments, the protecting group may be a protein moiety. In certain embodiments, wherein the protecting group is a protein, the protein moiety may be produced as a fusion protein with the at least one recombinant modified haemoglobin chain subunit. Alternatively, the protein moiety and the at least one recombinant modified haemoglobin chain subunit may be expressed separately or co-expressed and linked by chemical means such as by a chemical cross linker. Suitable chemical cross linkers will be known by those skilled in the art. By way of example cross linking agents may be one or more of glutaraldehyde, disparin derivatives, polyaldehydes, diphosphate esters, triphosphate esters.

In certain embodiments, the protein moiety is an antioxidant enzyme. By way of example the antioxidant enzyme may be a catalase and/or superoxide dismutase. In certain embodiments, the protein moiety is a human catalase and/or human superoxide dismutase. Without being bound by theory a protecting group may help prevent enzymatic or catalytic degradation of the conjugate.

Compositions and Uses

In a further aspect of the present invention, there is provided a composition comprising:
a conjugate protein comprising;
  a. at least one polymeric moiety; and
  b. at least one recombinant modified haemoglobin chain subunit comprising at least one or more of an alpha, a beta, a gamma or a delta chain subunit;
    wherein the at least one recombinant modified haemoglobin chain subunit comprises at least one modification for introducing at least one exogenous amino acid residue comprising at least one reactive thiol group to the at least one haemoglobin chain subunit for conjugation to the at least one polymeric moiety; and wherein the at least one polymeric moiety is conjugated to the at least one exogenous amino acid residue; and
  wherein, if the at least one recombinant chain subunit comprises a beta and/or gamma chain subunit, endogenous amino acid residue cysteine 93 is deleted or substituted with an amino acid residue which does not comprise a reactive thiol group; and
a pharmaceutically acceptable carrier or diluent.

In certain embodiments, the conjugate is a conjugate as described herein.

In a further aspect of the present invention, there is provided a composition comprising:
a recombinant modified multimeric protein comprising;
  a conjugate protein comprising;
    i. at least one polymeric moiety; and
    ii. at least one recombinant modified haemoglobin chain subunit comprising at least one or more of an alpha, a beta, a gamma or a delta chain subunit;
    wherein the at least one recombinant modified haemoglobin chain subunit comprises at least one modification for introducing at least one exogenous amino acid residue comprising at least one reactive thiol group to the at least one haemoglobin chain subunit for conjugation to the at least one polymeric moiety; and wherein the at least one polymeric moiety is conjugated to the at least one exogenous amino acid residue; and
  wherein, if the at least one recombinant chain subunit comprises a beta and/or gamma chain subunit, endogenous amino acid residue cysteine 93 is deleted or substituted with an amino acid residue which does not comprise a reactive thiol group; and
  at least one further haemoglobin chain subunit; and
a pharmaceutically acceptable carrier or diluent.

In certain embodiments, the recombinant modified multimeric protein is a recombinant modified multimeric protein as described herein.

In certain embodiments, the compositions of certain embodiments of the invention further comprise at least one reductant. In certain embodiments, the at least one reductant is Nicotinamide adenine dinucleotide phosphate (NADPH). In certain embodiments, the at least one reductant is Nicotinamide Adenine Dinucleotide (NADH). In certain embodiments, the reductant is one or more of ascorbate, NADP and/or NADH. Other suitable reductants will be known to those skilled in the art.

In certain embodiments, the compositions of certain embodiments of the present invention are pharmaceutical compositions and are for administration to a subject. In certain embodiments, the subject is a mammalian subject. In certain embodiments, the subject is a human.

In certain embodiments, the compositions of certain embodiments of the present invention are blood substitute compositions. A blood substitute composition is a composition which may be used to mimic and/or fulfil the functions of blood. Blood substitute compositions may include such components as plasma, serum albumin and other fluids of which are not derived from blood such as plasma volume expanders; these, may include for example crystalloid intravenous solutions. Other suitable blood substitute components will be known to those skilled in the art. The components of a blood substitute that is able to mimic bloods ability to carry and transfer oxygen may be referred to as an oxygen therapeutic. Thus, in certain embodiments the conjugates and compositions thereof as described herein, and recombinant modified multimeric proteins and compositions thereof as described herein of the present invention may be referred to as oxygen therapeutics.

Thus, in certain embodiments, the compositions of certain embodiments of the present invention are for use as oxygen therapeutics.

In certain embodiments, the compositions of certain embodiments of the present invention are resuscitation fluids. Resuscitation fluids are fluids that may be used to restore intravascular volume. Without being bound by theory resuscitation fluids may be broadly categorized into two main categories, colloid and crystalloid solutions. Colloid solutions are suspensions of molecules within a carrier solution that are relatively incapable of crossing a healthy semipermeable capillary membrane owing to the molecular weight of the molecules. Crystalloids are solutions of ions that are freely permeable but contain concentrations of salts such as sodium and/or chloride that determine the tonicity of the fluid. By way of example resuscitation fluids may include at least one or more of sodium, potassium, calcium, magnesium, chloride, acetate, lactate, malate, gluconate, bicarbonate or octanoate. Other suitable resuscitation fluid components will be known by those skilled in the art In certain embodiments, the conjugates and compositions thereof of embodiments of the present invention are for use as a medicament.

In certain embodiments, the recombinant modified multimeric proteins and compositions thereof of embodiments of the present invention are for use as a medicament.

Certain embodiments of the conjugates and compositions thereof as described herein, and recombinant modified multimeric proteins and compositions thereof as described herein may be for use as a bridge to red blood cell transfusion. The term "bridge to red blood cell transfusion" as used herein refers to when red blood cell transfusion is a viable treatment but is delayed. Therefore, the use of certain embodiments of the conjugates and compositions thereof as described herein, and recombinant modified multimeric proteins and compositions thereof as described herein may help to prevent and/or treat ischemia and/or hypoxia that may occur, until a red blood cell transfusion can be performed. By way of example certain embodiments of the conjugates and compositions thereof as described herein and recombinant modified multimeric proteins and compositions thereof as described herein may be used in situations when no red blood cells are readily available, such as on a battlefield or in remote areas and/or when suitable red blood cells cannot be readily matched to the blood type of a subject in need thereof or when amounts of red blood cells are not sufficient for treatment such as when treating large numbers of subjects in need thereof.

Thus, in certain embodiments, the conjugates and compositions thereof of embodiments of the present invention are for use in the treatment of ischemia and/or hypoxia.

In certain embodiments, the recombinant modified multimeric protein and compositions thereof of embodiments of the present invention for use in the treatment of ischemia and/or hypoxia.

Ischemia is a lack of and/or reduced blood flow to an organ or tissue. Ischemia may be caused by a blockage within one or more blood vessels or due to external compression of one or more blood vessels. By way of example a blockage within a blood vessel may be a thrombus or atherosclerosis. Such blockages may be arterial blockages or venous blockages, other blockages will be known by those skilled in the art and may cause what is known in the art as arterial or venous insufficiency. By way of example external compression of a blood vessel may be caused by trauma which may induce swelling and/or inflammation therefore constricting the blood vessels or may be caused by an external object and/or internal tissue such as a tumour or cancerous growth or inflamed organ applying pressure to a blood vessel. Ischemia may also occur when blood loss occurs such as due to acute haemorrhage, due to trauma or during surgical procedures. Types of ischemia will be known by those skilled in the art but non-limiting examples include myocardial ischemia, cerebral ischemia, limb ischemia, mesenteric ischemia and/or cutaneous ischemia.

As red blood cells normally carry 98% of the oxygen in blood to cells, tissues and organs, ischemia may lead to hypoxia. Hypoxia is a lack of and/or reduced amount of oxygen being transported to cells, tissues or organs and may be defined as a decrease in the oxygen tension within a tissue below normal functioning levels. Oxygen tension is a measure of the partial pressure of oxygen within blood and/or a tissue. Oxygen transfer from blood vessels, such as a capillary to associated tissue or cells may be characterised in terms of oxygen flux. As used herein the term "oxygen flux" refers to the mass of oxygen transported through a blood vessel per unit of time. When blood flow is reduced as may be caused for example by blood loss (haemorrhage), ischemia and/or shock (e.g. volume deficiency shock, anaphylactic shock, septic shock or allergic shock) a reduced amount of red blood cells flow through the blood vessel and therefore the oxygen flux decreases, therefore leading to a decrease in the transfer of oxygen to associated cells or tissue thereby resulting in hypoxia and in some cases anoxia, which is characterised as a tissue condition wherein no measurable oxygen is present. Both hypoxia and anoxia may lead to death of cells and/or tissue (necrosis). Thus, certain embodiments of the conjugates and compositions thereof of the present invention may be for use in the treatment and/or prevention of hypoxia and/or anoxia and therefore may be for use in the prevention of necrosis.

Thus, in one aspect of the present invention, there is provided a method of treating and/or preventing ischemia comprising administering to a subject in need thereof a pharmaceutically effective amount of a pharmaceutical composition comprising a:

a conjugate protein comprising;
   a. at least one polymeric moiety; and
   b. at least one recombinant modified haemoglobin chain subunit comprising at least one or more of an alpha, a beta, a gamma or a delta chain subunit;
     wherein the at least one recombinant modified haemoglobin chain subunit comprises at least one modification for introducing at least one exogenous amino acid residue comprising at least one reactive thiol group to the at least one haemoglobin chain subunit for conjugation to the at least one polymeric moiety; and wherein the at least one polymeric moiety is conjugated to the at least one exogenous amino acid residue; and
     wherein, if the at least one recombinant chain subunit comprises a beta and/or gamma chain subunit, endogenous amino acid residue cysteine 93 is deleted or substituted with an amino acid residue which does not comprise a reactive thiol group.

In certain embodiments, the conjugate is a conjugate as described herein.

In further aspect of the present invention, there is provided a method of treating and/or preventing ischemia comprising administering to a subject in need thereof a pharmaceutically effective amount of a pharmaceutical composition comprising:

a recombinant modified multimeric protein comprising;
   a conjugate protein comprising;
     i. at least one polymeric moiety; and
     ii. at least one recombinant modified haemoglobin chain subunit comprising at least one or more of an alpha, a beta, a gamma or a delta chain subunit;
     wherein the at least one recombinant modified haemoglobin chain subunit comprises at least one modification for introducing at least one exogenous amino acid residue comprising at least one reactive thiol group to the at least one haemoglobin chain subunit for conjugation to the at least one polymeric moiety; and wherein the at least one polymeric moiety is conjugated to the at least one exogenous amino acid residue; and
     wherein, if the at least one recombinant chain subunit comprises a beta and/or gamma chain subunit, endogenous amino acid residue cysteine 93 is deleted or substituted with an amino acid residue which does not comprise a reactive thiol group; and
   at least one further haemoglobin chain subunit.

In certain embodiments, the recombinant modified multimeric protein is a recombinant modified multimeric protein as described herein.

Certain embodiments of the conjugates and compositions thereof as described herein, and recombinant modified multimeric proteins and compositions thereof as described herein may be for use as an alternative to red blood cell transfusion. By way of example certain embodiments of the conjugates and compositions thereof as described herein and recombinant modified multimeric proteins and compositions thereof as described herein may be used when a subject in need thereof rejects a red blood cell transfusion, such as for religious reasons and/or when repetitive red blood cell transfusions over a substantial time period are required, such as subject suffering from anaemia or anaemia related disease and/or where no suitable red blood cells are available such as in developing countries.

Certain embodiments of the conjugates and compositions thereof as described herein, and recombinant modified multimeric proteins and compositions thereof as described herein may be for use in the protection and/or maintenance of the functioning of organs at risk due to medical conditions and/or surgical procedures e.g. the brain, spinal cord, heart, kidney or gut.

Certain embodiments of the conjugates and compositions thereof as described herein, and recombinant modified multimeric proteins and compositions thereof as described herein may be for use in the maintenance of ex vivo organs and/or tissues. By way of example transplant organs wherein oxygen content is needed to be maintained to ensure the organ is in an acceptable condition to be transplanted into a subject in need thereof. By way of example organs may include at least one of heart, liver, lung or kidney.

The terms "patient", "subject" and "individual" may be used interchangeably and refer to either a humans or non-human mammal. In certain embodiments, the subject is a human.

As used herein an "effective" amount or a "therapeutically effective amount" of a protein refers to a nontoxic but sufficient amount of the protein to provide the desired effect. The amount that is "effective" will vary from subject to subject, depending on the age and general condition of the individual, mode of administration, and the like. An appropriate "effective" amount in any individual case may be determined by one of ordinary skill in the art using routine experimentation.

The therapeutically effective amount of the conjugates and recombinant modified multimeric proteins and compositions thereof as described herein will depend on the route of administration, the type of subject being treated, and the physical characteristics of the specific subject under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. Certain embodiments of the conjugates and recombinant modified multimeric proteins and compositions thereof of the present disclosure may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e. not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments.

Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

Certain embodiments of the conjugates and recombinant modified multimeric proteins and compositions thereof as described herein may be for use in cell, tissue, or organ culturing and/or preservation. In certain embodiments, the conjugates and compositions thereof may be used alone or in addition to one or more further oxygen carrying proteins and/or in addition to a culture and/or preservation media suitable for cell culture, tissue culture and/or organ culture and/or tissue and/or organ perfusion. Without being bound by theory, certain embodiments of the conjugates as described herein, and recombinant modified multimeric proteins as described herein may help to increase the oxygen transported to said cells, tissues and/or organs and therefore increase the probability of maintaining healthy normal living cells, tissue or organs.

In certain embodiments, the conjugates and compositions thereof as described herein, and recombinant modified multimeric proteins and compositions thereof as described herein may also extend the lifetime of cultured cells, tissues or organs. Thus, in certain embodiments, there is provided a composition which comprises a conjugate described herein and a cell culture media. In certain embodiments, the cell culture media is a liquid medium and may be selected from Viaspan®, 1 IGL®, Celsior®, SCOT Maco®, BMPS Belzer®, Custodiol® (HTK), Euro-Collins®, Soltran®, Perfadex®, Ringer lactate and/or Plegisol®, Dulbecco's Modified Eagle Medium/Nutrient Mixture F-12, minimal essential media, Roswell Park Memorial Institute medium 1640 or 199 and/or any medium composition suitable for preservation of organs, tissues, or organ cells or tissue, or suitable for organ or tissue perfusion.

EXAMPLES

Methods

Protein PEGylation

PEGylation buffer (100 mM HEPES, 100 mM NaCl, 1.2 mM Na phosphate, 1 mM ETDA, pH 7) was bubbled with carbon monoxide or nitrogen before addition of protein samples. For each sample, absorption spectra were collected in the range of 450-700 nm to determine protein concentration and oxidation state. First, each sample was diluted with CO-equilibrated buffer (5 µl of stock protein samples+115 µl CO-equilibrated buffer) to determine the fraction of oxidized Hb. Then, dithionite was added to the sample to remove oxidized haemoglobin, thus obtaining a pure carbon monoxide haemoglobin (HbCO). Another spectrum was acquired to determine protein concentration by using the molar extinction coefficient of HbCO. All the samples were brought to 1 mM concentration (haem) with CO or nitrogen equilibrated PEGylation buffer. The final volume of the samples PEGylated was 200 µl. 20 kDa MAL-PEG (MeO-PEG-mal, Iris Biotech) was added to the protein solutions in a 12:1 ratio PEG:Hb tetramer. The samples were left to react at 25° C. for 60 minutes. MAL-PEG stock solution (10 mM) was prepared from powder just before reacting with Hb. The reaction was quenched by the addition of 2 µl of 0.9M Cys solution to each sample. Unreacted reagents and unmodified haemoglobin was removed by dialysis (100 kDa MWCO centrifuge filters). A colored flow through was observed for all samples due to unmodified and/or monoPEGylated Hb. After dialysis, absorption spectra were collected from the samples to evaluate the protein concentration and oxidation state. Samples were stored at −80° C.

Non-homogenous PEGylation of haemoglobin's (i.e. wild-type rHbA of FIG. 1 right hand panel) was performed using 2-imino thiolane (IMT) to create new reactive —SH groups on surface —NH2 (lysine) residues. The protein was subsequently PEGyated with a 5.6 kDa maleimide-PEG (e.g. see Portoro, I., Kocsis, L., Herman, P., Caccia, D., Perrella, M., Ronda, L., Bruno, S., Bettati, S., Micalella, C., Mozzarelli, A., Varga, A., Vas, M., Lowe, K. C., and Eke, A. (2008) Biochim. Biophys. Acta 1784, 1402-1409).

Cysteine Reactivity

Sodium p-hydroxy mercury benzoate (PMB) was freshly prepared prior each experiment as follows: PMB was dissolved in a small volume of 1M sodium hydroxide. Next, a drop of acetic acid was added. Finally, the PMB solution was cleared by addition of 1M sodium hydroxide dropwise until cloudiness disappeared. Hb solutions were diluted to 20 µM in 70 mM sodium phosphate buffer (pH 7.2) into 1 mL quartz cuvettes and CO was bubbled through the sample. Absorption spectra were recorded after each addition of PMB (1 µM).

Oxygen Binding Measurements p50 measurements were carried out by diluting the stock Hb solutions in 100 mM HEPES, 100 mM sodium chloride, 1.2 mM sodium phosphate, 1 mM EDTA, pH 7.0. The final protein concentration was 100 µM (haem). Oxygen equilibrium curves were measured at 25° C., as previously reported (Ronda et al., Methods in Enzymology 437, 311-328). For each sample, the absorption spectrum (equilibrated in air) was collected immediately after thawing. Ascorbate and catalase were added to the solution before titrations to reduce met-Hb and to limit its formation during titration. The samples were deoxygenated using a helium flow and then equilibrated with different oxygen partial pressures. A complete titration required about 5 hours.

MALDI TOF Mass Spectrometry

Mass spectra were acquired in the m/z range 10-40 kDa using a 4800 MALDI TOF/TOF (SCIEX) instrument. Protein samples were mixed with 10 mg/mL α-cyano-4-hydroxycinnamic acid (HCCA) matrix solubilized in acetonitrile 75% (v/v)—trifluoracetic acid 2.5% (v/v) in 1:9 ratio (v/v) and 1 µL was spotted onto MALDI plate. Spectra were obtained mediating 500 laser shots in linear positive ion mode.

Autoxidation Rate

Autoxidation of 10 µM oxyHb in 70 mM sodium phosphate buffer, pH 7.2, at 37° C., was monitored spectrophotometrically. The oxyHb concentrations were calculated using the extinction coefficients of 125,000 (415 nm) and 14,600 (577 nm) $M^{-1}$ $cm^{-1}$. Rate constants of time courses (406-500 nm) were determined by fitting to an exponential function using the Microsoft Excel Solver algorithm (minimising the least squares difference between the data points and the fit).

Haem Release Rate

His-tagged sperm whale (SW) myoglobin (Mb) (H64Y/V67F) was expressed, purified and haem removed as described previously (Silkstone et al. (2016) Engineering tyrosine electron transfer pathways decreases oxidative toxicity in haemoglobin: implications for blood substitute design. Biochemical Journal 473). MetHb (3 µM) was incubated with 30 µM apo SW Mb (H64Y/V67F) in 0.15M sodium acetate, 0.4M sucrose, pH 5 at 37° C. and reactions monitored using a Tecan Infinite M200Pro plate reader. Rate constants of time courses (600-650 nm) were determined by fitting to an exponential function using the Microsoft Excel Solver algorithm (minimising the least squares difference between the data points and the fit)

Presence of Accessible Thiol Groups as Assessed by Binding of p-Mercuribenzoate (PMB)

Purified modified-carboxy haemoglobins were incubated with increasing concentrations of PMB in 70 mM sodium phosphate buffer pH 7.2 and interaction of free thiol groups with PMB was monitored by measuring the absorbance at 250 nm-306 nm.

Results

Tested proteins included:

A12: HbA comprising the alpha chain modification αA19C (SEQ ID NO: 5) and the beta chain modification βC93A (SEQ ID NO: 8); and A13: HbA comprising no alpha chain modifications (SEQ ID NO: 2) and the beta chain modifications βA13C and βC93A (SEQ ID NO: 18).

Control proteins included:

A0: Wild-type native (i.e. not recombinant) HbA;

A1: Wild-type recombinant HbA; and

A11: HbA comprising no alpha chain modifications (SEQ ID NO: 2) and the beta chain modification βC93A (SEQ ID NO: 8).

Conjugation

FIG. 1 illustrates denaturing SDS-PAGE gels of haemoglobin. It is noted that as the gel is a denaturing SDS-PAGE gel the α- and β-subunits dissociate into monomers, appearing on the gel as a band at approximately 17 kDa (M). The band located at approximately 35 to 40 kDa corresponds to dimers (D) that are covalently joined subunits that may be formed due to unwanted side reactions leading inter-subunit disulphide bridge formation and/or oxidatively damaged covalently bound dimers. Due to changes in electrophoretic mobility induced by addition of the 20 kDa PEG moiety to the monomeric alpha (A12) or beta subunit (A1 and A13), each monomeric PEGylated subunit displays a molecular weight of approximately 50-65 kDa upon SDS-PAGE analysis (1P).

It can be seen from FIG. 1 that only a single a 20 kDa maleimide PEG moiety is conjugated to the alpha subunit of adult haemoglobin (HbA) A12 (conjugated A12 is referred to herein as PEG-A12) (i.e. the PEGylation is homogenous). This is confirmed by the SDS-PAGE gel shown in FIG. 1A (left hand image), in which the presence of a single band in lane 3 (1P) corresponds to PEG-A12 having greater apparent molecular weight than that of the α-chain subunit/β-chain dimer without a PEG conjugate (band D) and the alpha and beta subunit monomers (band M)

Conjugation at a single site is further confirmed by comparison of FIG. 1B (right hand image) to FIG. 1A. FIG. 1B shows SDS-PAGE analysis of WT recombinant HbA (rHbA) (also referred to as A1) that has been PEGylated using prior art methods that conjugates PEG via lysine residues. It can be seen that a number of bands with greater MW than that of the subunit monomers (M) are present. Each band (1P to 8P) in lane 3 of FIG. 1B correspond to an increasing number of PEG moieties being conjugated to A1.

Figure 2A:
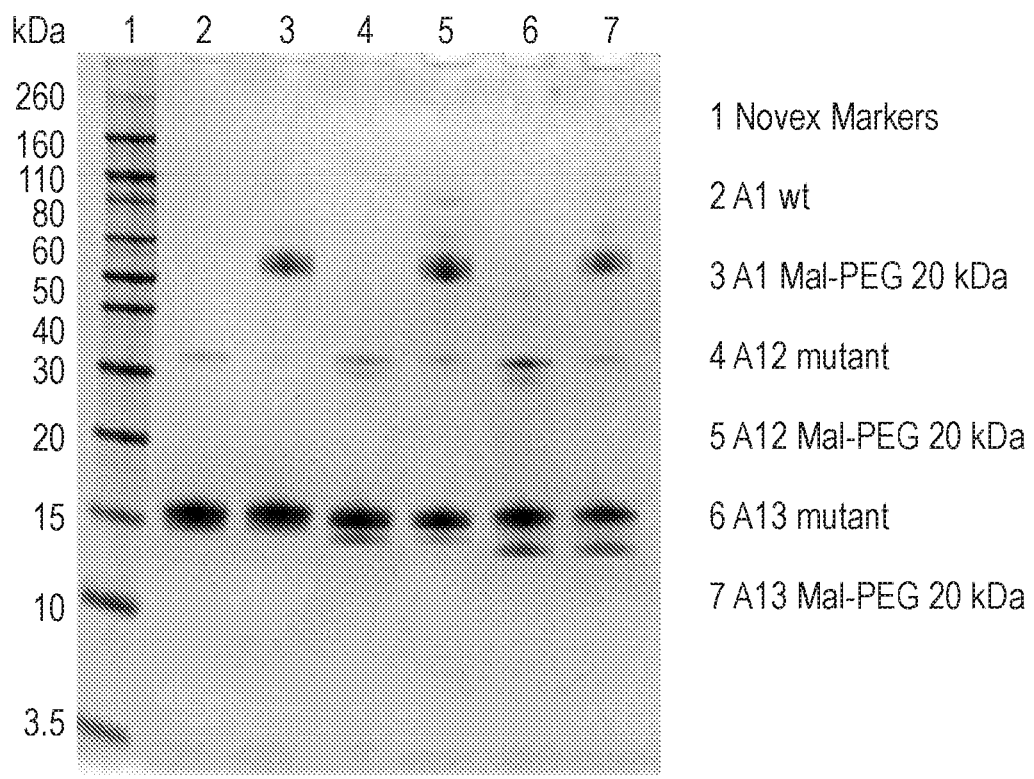
FIGS. 2A (top image) and B (bottom image) show SDS-PAGE gels showing species formed before and after conjugation using a 20 kDa maleimide PEG moiety: on the gel M relates to molecular weight markers; A1 (recombinant WT HbA reactive —SH at βC93); A11 (βC93A); A12 (αA19C/βC93A); and A13 (βA13C/βC93A). No PEGylation is seen in the control mutant lacking a free —SH residue (A11). A12 and A13 form a greater amount of homogeneously conjugated product as shown by the band of greater intensity at approximately 50 kDa. It is noted that the gels separate non-covalently bound Hb subunits, therefore the wild type Hb alpha and beta chain subunits show as a band at 17 kDa (bottom of gel). PEG interacts with SDS and changes the electrophoretic mobility of Hb such that the 17 kDa alpha or beta subunit conjugated to a 20 kDa PEG runs at approximately 50 kDa. Thus, complete homogenous PEGylation of A1, A12 or A13 would be seen as a band at 17 kDa for unconjugated chain subunits and a band of equal intensity at 50 kDa corresponding to PEG conjugated chain subunits. Note that the small bands seen near 30 kDa are due to undesirable side reactions and represent either oxidatively damaged covalently bound dimers or dimers with intersubunit disulfide bridges.
Figure 2B:
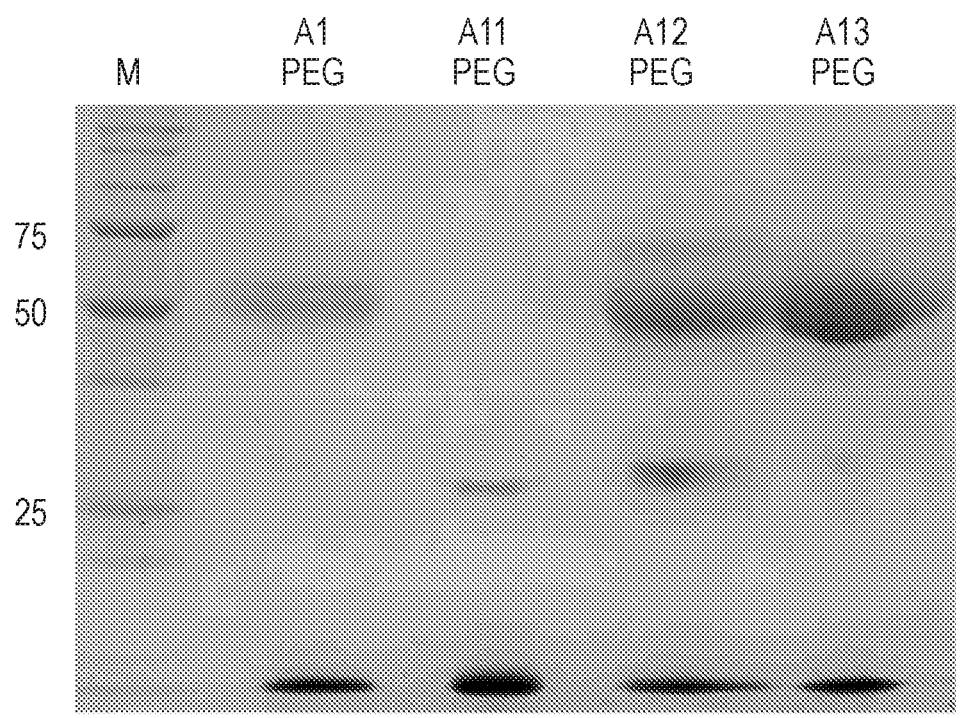

The efficiency of conjugation was tested by determining the intensity of bands seen upon SDS-PAGE analysis of PEGylated modified haemoglobins using densitometry. Densitometry measurements of were taken from the SDS-PAGE gels shown in FIGS. 2A (upper image) and 2B (enhanced lower image). In FIG. 2B it can be seen that for the PEG-A12 (lane 4) and PEG conjugated A13 (PEG-A13) (lane 5) that the bands corresponding to singularly PEGylated monomers (1P) have higher intensity than that of the 1P band corresponding to the controls A1 (lane 2) and A11 (lane 3). The lack of a band corresponding to PEGylated monomers for A11 (lane 3 FIG. 2B) confirms that the site of PEGylation is the modified amino acid residue αA19C or βA13C, as A11 does not have the cysteine residue at position 93, and so therefore lacks any available thiol containing moieties for conjugation to the PEG moiety.

The data shown in FIG. 2B indicates that the number of monomers that have been PEGylated for the A12 and A13 mutants is greater than that of the controls, therefore showing an increased efficiency of conjugation. The lack of a 1P band for PEGylated A11 (lane 3 of FIG. 2B) indicates that it is the modifications αA19C or βA13C introducing a thiol group (cysteine) that provides a site for conjugation.

Figure 3:
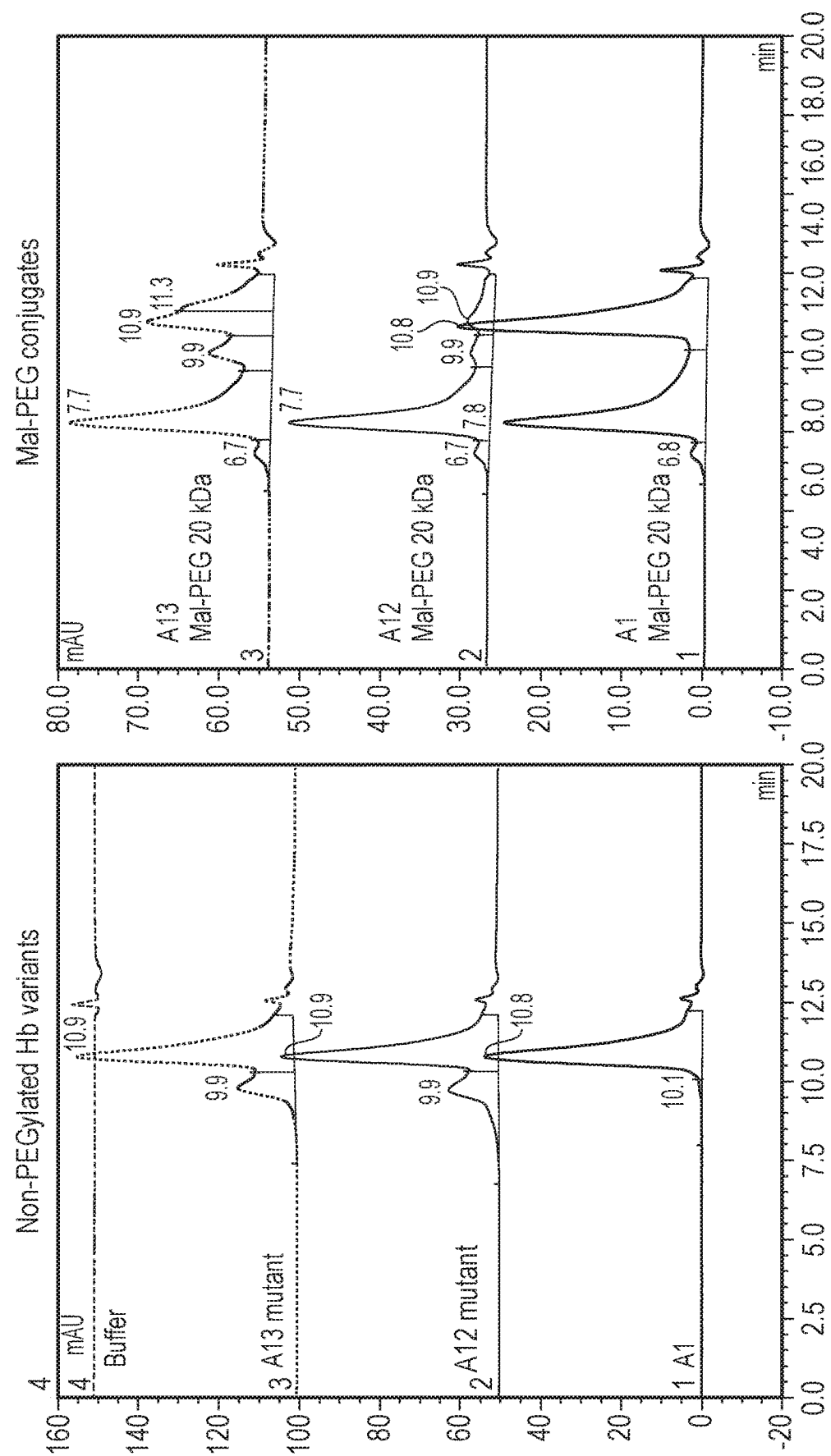

Size exclusion chromatography (SEC) analysis showed that A12 had the highest levels of homogenous PEGylation. FIG. 3A (left hand image) shows the unPEGylated proteins and FIG. 3B (right hand image) shows the PEGylated proteins. It can be seen from FIG. 3B that A1PEG shows two distinct peaks. The peak at approximately 7.7 minutes corresponds to PEGylated α/β subunit dimers. The peak seen at approximately 10.9 minutes corresponds to un-PEGylated α/β subunit dimers.

It can be seen that for modified protein A13 a distinct peak is present at approximately 7.7 minutes as well as a distinct peak at approximately 10.9 minutes. The peak at approximately 10.9 minutes is less than that seen for A1 indicating that the homogeneity of the PEGylated product is improved. A number of less defined peaks can also be discerned from the plot indicating that other species may also have been formed during the conjugation reaction.

In comparison, A12 shows a defined single peak at approximately 7.7 minutes but a much lower peak than that seen for both A1 and A13 at approximately 10.9 minutes, indicating that modified protein A12 is more efficiently and homogenously PEGylated than both A2 and modified protein A13.

Figure 4:
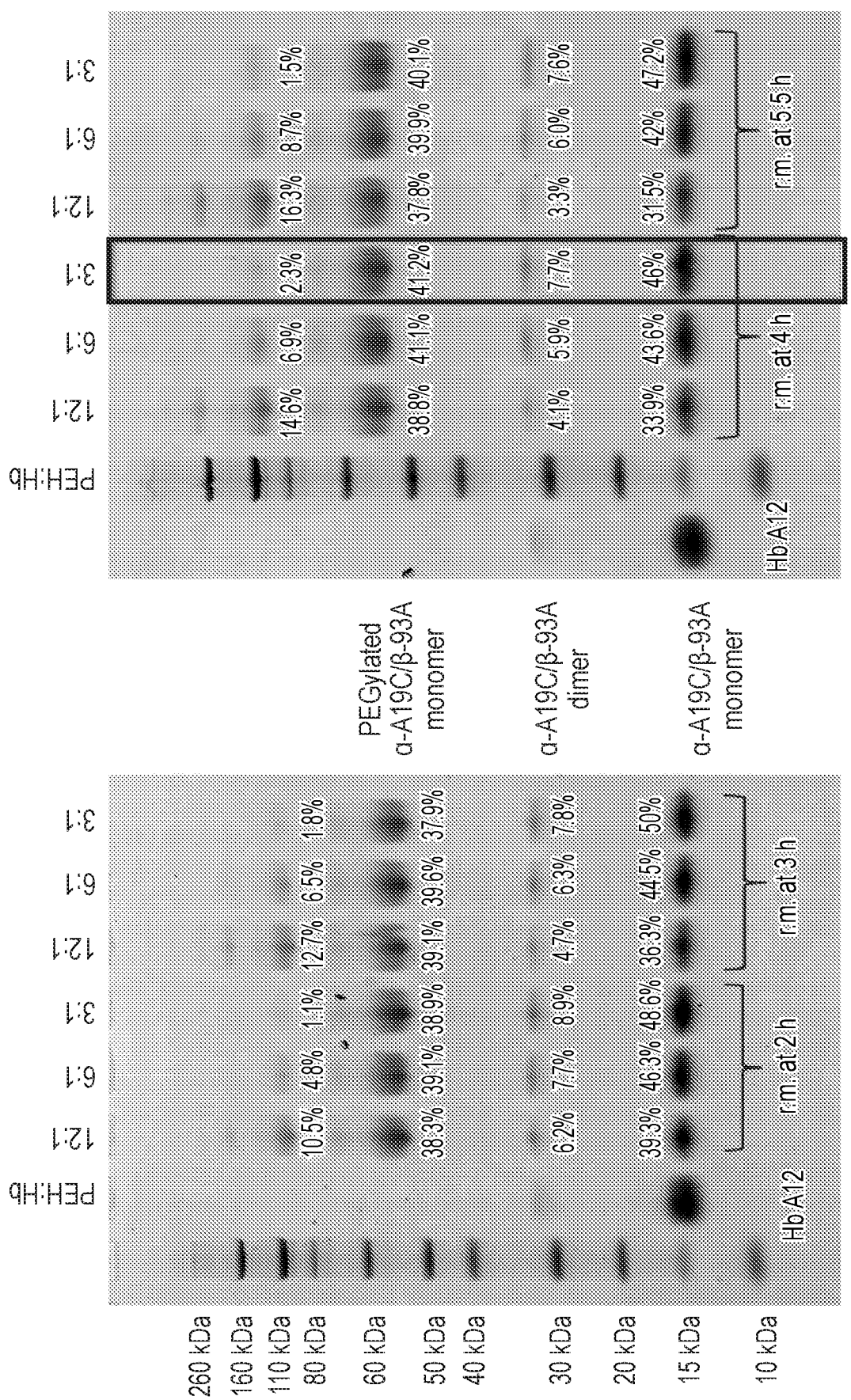

As modified protein A12 proved to be conjugated more homogenously and more efficiently than modified protein A13, conjugation efficiency was further investigated, by varying incubation time and ratio of PEG to protein. It can be seen from FIG. 4 that for modified protein A12 the maximum efficiency of conjugation was achieved at a PEG: protein ratio of 12:1 with an incubation time of 3 hours. This provided a conjugation efficiency of 41.3%. This value of conjugation efficiency represents a high level of homogeneity as only the α-subunit, comprising the modification αA19C, has a site for conjugation of the PEG moiety. Therefore, if there was "perfectly" homogenous PEGylation in the case of A12, (i.e. all the available PEGylation sites were PEGylated and no other sites were PEGylated) one would expect see an intensity of 50% as 50% of the monomers are α-subunits (with a PEGylation site) and 50% of the subunits are β-subunits, comprising the modification βC93A, and therefore have no available site for PEGylation.

Figure 5:
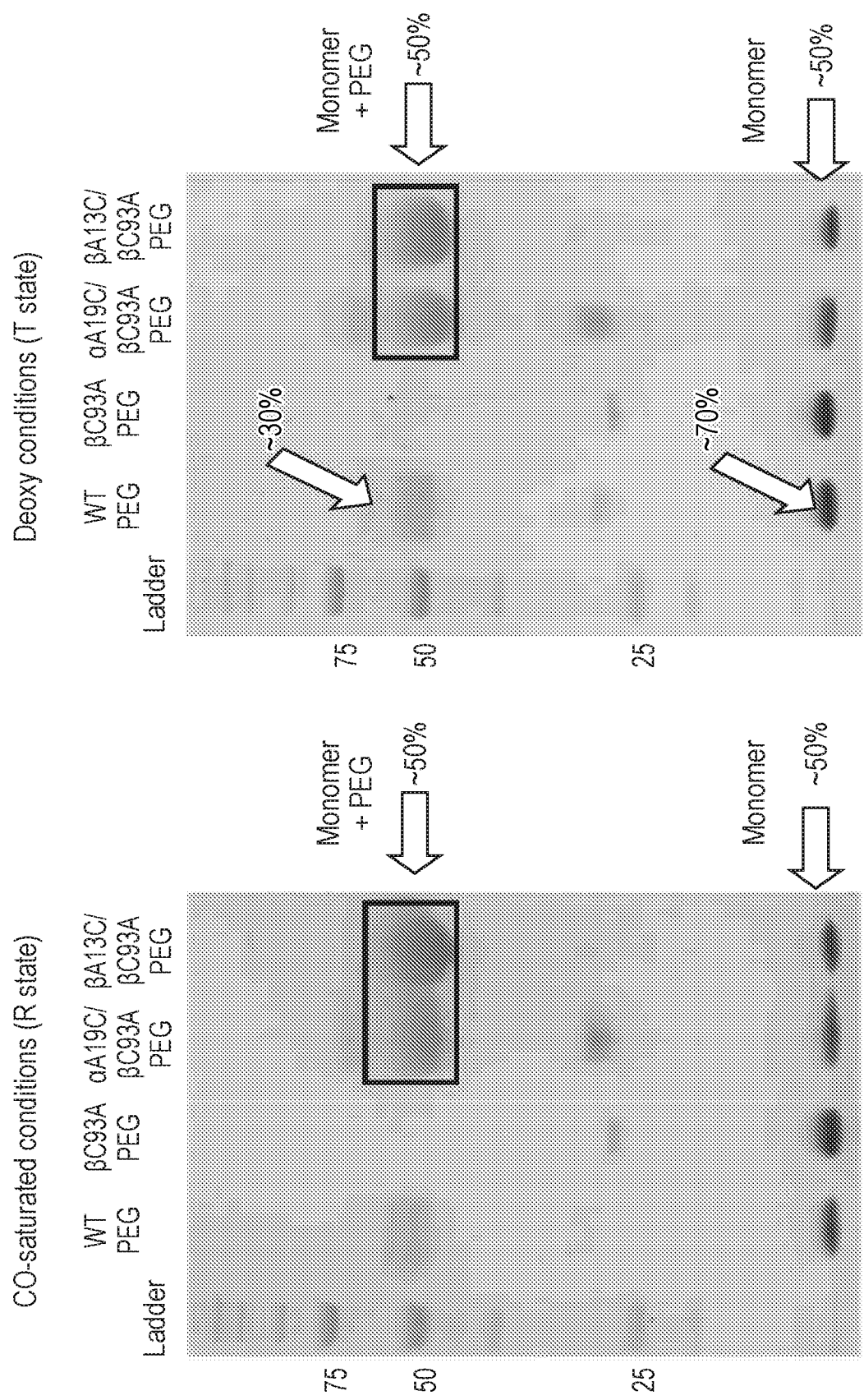
FIG. 5 shows SDS-PAGE gels comparing conjugation of 20 kDa maleimide-PEG to the carbon monoxide bound (R-state) and deoxy (T-state) form of the HbAs indicated. The presence and intensity of the band seen at approximately 50 kDa confirms more efficient conjugation of PEG to A12 and A13 compared to A1 under different conformational forms of the enzyme. As expected A11, lacking a free —SH group shows no PEGylation.

Conjugation efficiency was also tested on the modified proteins A12 and A13 and the control proteins A1 and A11 both in CO-saturated conditions (protein in R-state) and deoxy conditions (protein in T-state). It can be seen from FIG. 5 that for A1 a conjugation efficiency of approximately 30% was recorded. For both modified proteins A12 and A13, conjugation efficiency was approximately 50% in both the R-state and T-state. This result shows that highly efficient homogeneous conjugation can be achieved in either the T-state or the R-state.

In conclusion, modified protein A12 shows the highest amount of homogeneity upon conjugation in comparison to both control proteins A11 and A1 as well in comparison to the modified protein A13. A12 conjugation also shows a relatively high efficiency of PEGylation greater than that seen for A1 and A13. It can therefore be concluded that the modification αA19C provides a site for highly efficient and homogeneous PEGylation.

Oxygen Binding, Autoxidation and Stability

Firstly, the effect of modifications without conjugation to a PEG moiety on autoxidation rate of oxy-haemoglobin to met-haemoglobin was tested for modified proteins A12 and A13 in comparison to the control proteins A1, A11 and A0. It can be seen from FIG. 6A that A13 has a similar rate of autoxidation as that seen for the controls A11 and A1 and A0. In comparison to the controls and modified protein A13, modified protein A12 has a decreased autoxidation rate.

The data indicates that the modification αA19C provides an improvement in the autoxidation rate of HbA.

In relation to haem release (FIG. 6B), which provides an indication of stability of the protein, modified protein A12 shows improved (decreased) haem release in comparison to both control proteins A1 and A0, whereas modified protein A13 shows a worsened (increased) rate of haem release.

The data shows that the introduction of a new reactive thiol moiety unalters or improves autoxidation properties and stability.

Next the oxygen binding properties, Hill's coefficient and p50, of the modified proteins A12 and A13 conjugated and unconjugated to PEG were tested in comparison to control protein A1 conjugated and unconjugated to PEG. Results were calculated from the graph shown in FIG. 7 and are shown in Table 2 below.

TABLE 2

| Protein | P50 before PEG (mmHg) | P50 after PEG (mmHg) | Hill coefficient before PEG | Hill coefficient After PEG |
|---|---|---|---|---|
| A1 WildType (β-C93) | 5.0 ± 0.3 | 3.8 ± 0.2 * | 1.7 ± 0.2 | 1.9 ± 0.2 |
| A13 β-A13C/β-C93A | 4.2 ± 0.2 | 4.6 ± 0.2 | 1.9 ± 0.3 | 2.0 ± 0.2 |
| A12 α-A19C/β-C93A | 4.4 ± 0.2 | 4.1 ± 0.2 | 1.6 ± 0.2 | 1.6 ± 0.1 |

* $p < 0.05$ compared to pre-PEGylated value.

In the case of A1, PEGylation of amino acid residue β-C93 causes a decrease in oxygen binding affinity (p50) and has a slight but insignificant effect on cooperativity of oxygen binding (Hill coefficient). For both modified proteins A12 and A13 PEGylation at either modified amino acid residues α-19C or β-13C has no significant effect on oxygen binding efficiency or cooperativity.

Figure 8A:
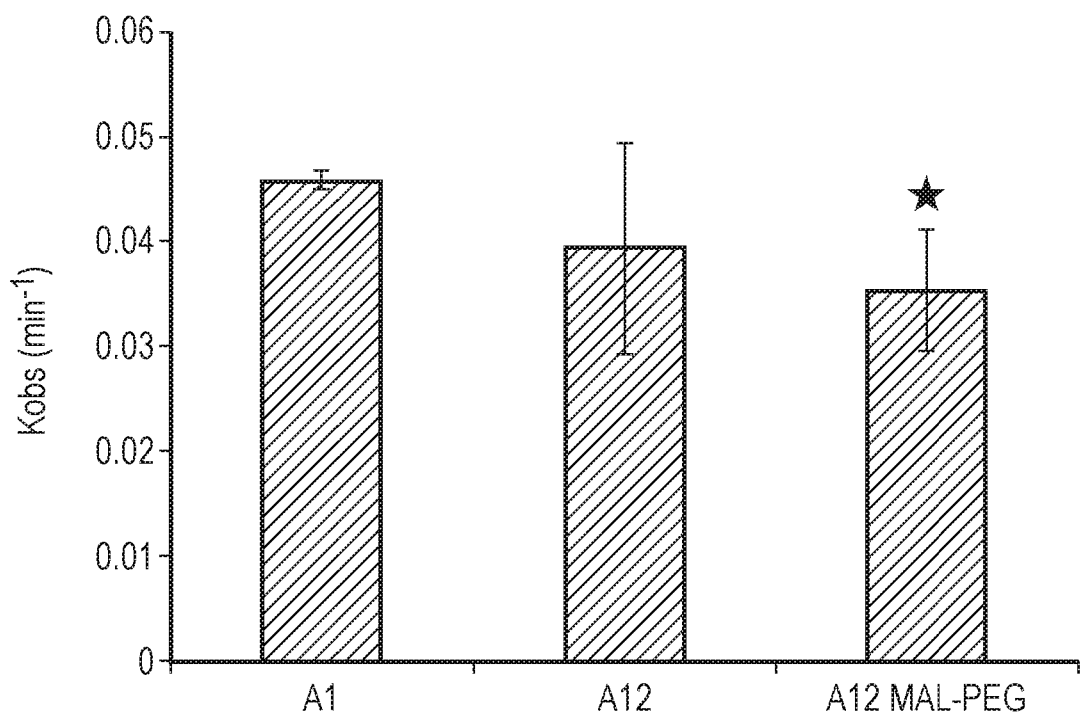
FIGS. 8A and 8B are graphs showing: A) Haem release data for un-PEGylated A1, un-PEGylated A12 and PEGylated A12. PEGylated A12 has a lower level of haem release in comparison to un-PEGylated A1 and un-PEGylated A12. B) Autoxidation data for A1, un-PEGylated A12 and PEGylated A12. PEGylated A12 has a lower rate of autoxidation in comparison to un-PEGylated A1 and un-PEGylated A12.
Figure 8B:
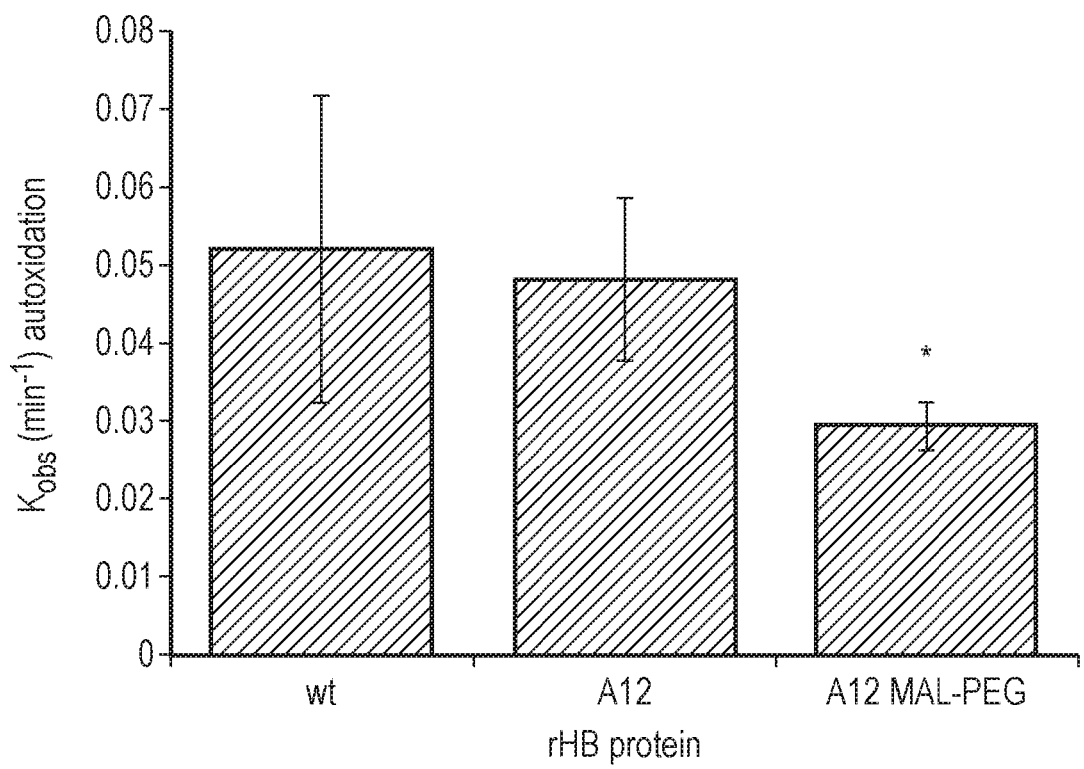

The haem release rate and autoxidation rate of PEG-A12 is shown in FIGS. 8a and 8b respectively. It can be seen that in comparison to both control protein A1 and unPEGylated A12, PEG-A12 has both an improved (decreased) rate of haem release and improved (decreased) rate of autoxidation.

It can be concluded that the modifications present in A12 do not alter, and in certain cases improve, the properties of the protein. Upon conjugation to a polymeric moiety, unlike control protein A1, there is no effect on oxygen binding properties of A12 or A13. It can also be seen that upon conjugation to a polymeric moiety the stability and rate of autoxidation of A12 improves.

Effects of Multiple Modifications

In order to determine whether the modification αA19C causes any effects on the properties instilled by other modifications (such as modifications to improve recombinant production and/or purification, decrease nitric oxide scavenging, increase ferryl and/or ferric reduction and decrease lipid oxidation) the modification αA19C was introduced into the alpha chain subunit in combination with further alpha chain subunits and formed into tetrameric HbA or HbF comprising one or more beta or gamma chain subunits comprising one or more further modifications.

The tested proteins included:

A49: HbA comprising the alpha chain modifications αV1M, αA19C and αL29F (SEQ ID NO: 7) and the beta chain modifications βV1M, βV67F, βT84Y and βC93A (SEQ ID NO: 9); and F48: HbF comprising the alpha chain modifications αV1M, αA19C and αL29F (SEQ ID NO: 7) and the gamma chain modifications γG1M, γV67F, γL96Y and γC93A (SEQ ID NO: 11 or SEQ ID NO: 13).

Firstly, the ability to conjugate a polymeric moiety to the introduced thiol groups in A25 and F49 was tested by monitoring the change in absorbance of p-mercuribenzoate (PMB) upon reaction with the introduced thiol moiety.

Figure 9A:
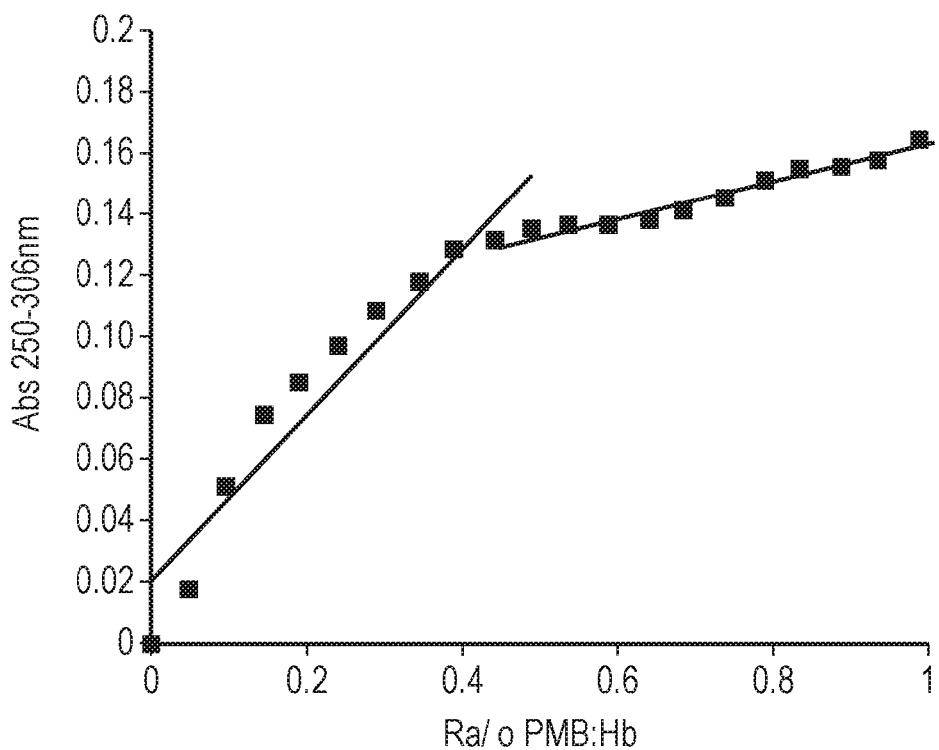
FIGS. 9A and B show change in absorbance of p-mercuribenzoate (PMB) upon reaction with the introduced reactive thiol group introduced by the modification αA19C for the modified HbAs A49 and F48: As with the "parent" mutation, A12, both A49 and F48 have reactive —SH residues as determined by the absorbance change caused by the reaction of the —SH reactive reagent p-mecuribenzoate (PMB) to the CO form of haemoglobin. A ratio of 0.5 PMB reacting per Hb tetramer indicates essentially 100% reactivity at the αA19C modification.
Figure 9B:
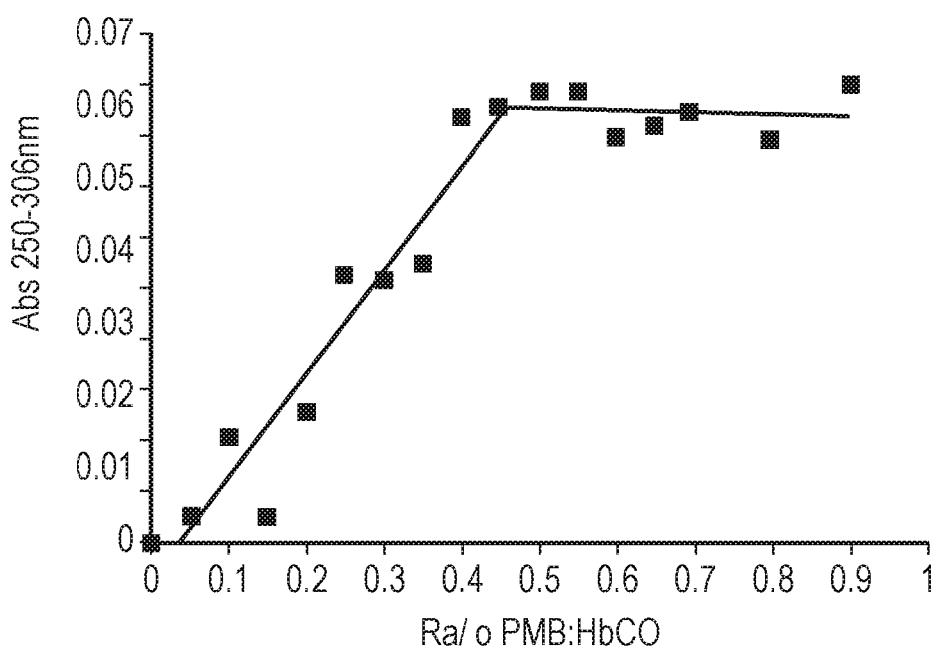

It can be seen from FIGS. 9A and B that absorbance at 250-206 nm increases with an increasing ratio of PMB to protein. This increase plateaus at around a ratio of 0.5 for both A49 and F48. This result indicates that the reactivity (and therefore ability of the introduced thiol group to bind a polymeric moiety) is approximately 100%.

CONCLUSIONS

It can be concluded from the data that the modification αA19C provides a highly efficient site for homogenous conjugation to a polymeric moiety in both HbA and HbF proteins and furthermore the efficiency of conjugation is not effected by the inclusion of further modifications.

It can also be concluded that a HbA comprising the modification αA19C (e.g. A12, A49 and F48) and conjugated via this modified amino acid residue have unaltered oxygen binding properties in comparison to an unconjugated form of the protein. Moreover, in comparison to wild-type (i.e. A0 and A1), unconjugated forms of the modified protein and as other modified proteins (i.e. A11 and A13) HbAs comprising the modification αA19C have improved autoxidation properties and stability.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A conjugate comprising:
   (a) at least one polymeric moiety comprising a polyethylene glycol molecule (PEG) or a polyalkylene glycol (PAG) and/or having a molecular weight of about 20,000 Daltons (20 kDa); and
   (b) at least one recombinant modified hemoglobin chain subunit comprising at least one alpha chain subunit;
   wherein endogenous amino acid residue alanine 19 of the alpha chain subunit is substituted with at least one exogenous amino acid residue comprising at least one reactive thiol group for conjugation to the at least one polymeric moiety;
   wherein the at least one polymeric moiety is conjugated to the at least one exogenous amino acid residue; and
   wherein, if the conjugate further comprises at least one additional recombinant modified hemoglobin chain subunit comprising a beta and/or gamma chain subunit, endogenous amino acid residue cysteine 93 of the beta and/or gamma chain subunit is deleted or substituted with an amino acid residue which does not comprise a reactive thiol group.

2. The conjugate according to claim 1, wherein the conjugate has at least one substantially unaltered or improved property selected from: at least one oxygen binding property; a rate of oxidation and/or reduction of a heme molecule of the recombinant modified hemoglobin chain subunit; and/or a stability of the recombinant modified hemoglobin chain subunit as compared to a reference protein, wherein said reference protein is a protein comprising the recombinant modified hemoglobin chain subunit without the at least one polymeric moiety.

3. The conjugate according to claim 2, wherein:
(i) the at least one oxygen binding property comprises a Hill coefficient of the conjugate;
(ii) the at least one oxygen binding property comprises a partial pressure of a gas required to achieve 50% saturation (p50) of the conjugate; or
(iii) the rate of oxidation and/or reduction of a heme molecule of the recombinant modified hemoglobin chain subunit is a rate of autoxidation of the heme group of the at least one recombinant modified hemoglobin chain subunit.

4. The conjugate according to claim 1, wherein:
(i) the stability of the at least one recombinant modified hemoglobin chain subunit is measured by a rate of release of a heme molecule from the at least one recombinant modified hemoglobin chain subunit;
(ii) the substitution at the amino acid residue alanine 19 of the alpha chain subunit is capable of an increase in the rate of oxidation of a heme molecule of the recombinant modified hemoglobin chain subunit of no more than about 5% as compared to a reference protein, wherein the reference protein is a protein comprising the recombinant modified hemoglobin chain subunit without the at least one polymeric moiety;
(iii) the at least one recombinant modified hemoglobin chain subunit is a mammalian hemoglobin chain subunit;
(iv) the at least one recombinant modified hemoglobin chain subunit is a human hemoglobin chain subunit;
(v) the amino acid residue cysteine 93 is substituted with alanine (A), glycine (G), valine (V) or leucine (L);
(vi) the substitution of the alanine 19 of the alpha chain subunit introduces the at least one exogenous amino acid to a position of the at least one recombinant modified hemoglobin alpha chain subunit, wherein the position is located on an outer surface of the conjugate when the conjugate is assembled in a secondary, a tertiary and/or a quaternary structure;
(vii) the substitution of the alanine 19 of the alpha chain subunit is configured to provide a conjugation efficiency of at least 30%;
(viii) the at least one reactive thiol group extends outwards from the outer surface of the conjugate when the conjugate is assembled in a secondary, tertiary and/or quaternary structure; or
(ix) the at least one exogenous amino acid residue comprising at least one reactive thiol group is a cysteine residue.

5. The conjugate according to claim 1, wherein
(i) the substitution of the alanine 19 of the alpha chain subunit comprises an αA19C modification; or
(ii) if the recombinant modified hemoglobin chain subunit comprises a beta chain subunit, amino acid residue 13 does not comprise a reactive thiol group, optionally wherein the endogenous amino acid residue 13 is alanine (A).

6. The conjugate according to claim 1, further comprising at least one further modification.

7. The conjugate according to claim 6, wherein:
(i) the at least one further modification comprises one or more of:
(a) one or more modifications for decreasing a nitric oxide reactivity;
(b) one or more modifications for introducing or enhancing reduction of at least one metallic ion associated with the at least one recombinant modified hemoglobin chain subunit thereby increasing a rate at which an oxidized form of the conjugate is capable of reoxygenation to an oxygen-binding form; or
(c) one or more modifications for improving production and/or purification of the at least one recombinant modified hemoglobin chain subunit; or
(ii) the at least one recombinant modified hemoglobin chain subunit comprises a hemoglobin alpha chain subunit and wherein the least one further modification is selected from one or more of:
(a) αV1M, αL29F and/or αL91Y.

8. The conjugate according to claim 1, wherein:
(i) the at least one recombinant modified hemoglobin chain subunit is further conjugated to at least one protecting group, optionally wherein the at least one protecting group is at least one antioxidant enzyme; or
(ii) the at least one recombinant modified hemoglobin chain subunit comprises an amino acid sequence having at least 80% sequence identity to an amino acid sequence selected from the group consisting of:
(a) SEQ ID NO:5;
(b) SEQ ID NO:6 and
(c) SEQ ID NO:7.

9. The conjugate according to claim 2, wherein:
the reference protein comprises an unconjugated form of the at least one recombinant modified hemoglobin chain subunit as described in claim 2.

10. A recombinant modified multimeric protein comprising at least one conjugate according to claim 1, wherein the conjugate comprises:
(a) at least one polymeric moiety;
(b) at least one recombinant modified hemoglobin chain subunit comprising at least one alpha chain subunit, wherein endogenous amino acid residue alanine 19 of the alpha chain subunit is substituted with at least one exogenous amino acid residue comprising at least one reactive thiol group for conjugation to the at least one polymeric moiety;
wherein the at least one polymeric moiety is conjugated to the at least one exogenous amino acid residue; and
(c) at least one additional recombinant modified hemoglobin chain subunit comprising a beta and/or gamma chain subunit, wherein endogenous amino acid residue cysteine 93 of the beta and/or gamma chain subunit is deleted or substituted with an amino acid residue which does not comprise a reactive thiol group.

11. A recombinant modified multimeric protein comprising;
(a) at least one conjugate according to claim 1; and
(b) at least one further hemoglobin chain subunit.

12. The recombinant modified multimeric protein according to claim 11, wherein the at least one further hemoglobin chain subunit comprises at least one alpha, at least one beta, at least one delta and/or at least one gamma hemoglobin chain subunit.

13. The recombinant modified multimeric protein according to claim 11, wherein:
   (i) the at least one further hemoglobin chain subunit is a mammalian hemoglobin chain subunit;
   (ii) the at least one further hemoglobin chain subunit is a human hemoglobin chain subunit; or
   (iii) the at least one further hemoglobin chain subunit comprises one or more modifications, optionally wherein one or more modifications are selected from one or more of:
   (a) one or more modifications for decreasing a nitric oxide reactivity;
   (b) one or more modifications for introducing or enhancing reduction of at least one metallic ion associated with the at least one further hemoglobin chain subunit thereby increasing a rate at which an oxidized form of the conjugate is capable of re-oxygenation to an oxygen-binding form;
   (c) one or more modifications for improving production and/or purification of the at least one further hemoglobin chain subunit; and/or
   (d) one or more modifications for preventing conjugation with the at least one polymeric moiety.

14. The recombinant modified multimeric protein according to claim 11 wherein:
   (i) the at least one further hemoglobin chain subunit is a hemoglobin alpha chain subunit and comprises one or more modifications selected from one or more of:
   (a) αV1M, αL29F and αL91Y;
   (ii) the at least one further hemoglobin chain subunit is a hemoglobin beta chain subunit and comprises one or more modifications selected from one or more of:
   (a) βC93A, βV1M, βV67F, βT84Y, βF85Y and/or βL96Y:
   (iii) the at least one further hemoglobin chain subunit is a hemoglobin gamma chain subunit and comprises one or more modifications selected from one or more of:
   (a) γ1G1M, γ1C93A, γd1L96Y and/or γ1V67F; and/or
   (b) γ2G1M, γ2C93A, γ2L96Y and/or γ2V67F;
   (iv) the at least one further hemoglobin chain subunit is non-conjugated;
   (v) the at least one conjugate comprises at least one recombinant modified hemoglobin chain subunit comprising an amino acid sequence having at least about 80% sequence identity to a sequence selected from the group consisting of:
   (a) SEQ ID NO:5;
   (b) SEQ ID NO:6; and
   (c) SEQ ID NO:7
   and wherein the recombinant modified multimeric protein further comprises at least one further haemoglobin chain subunit comprising an amino acid sequence having at least about 80% sequence identity to a sequence selected from one or more of:
   (d) SEQ ID NO:8
   (e) SEQ ID NO:9
   (f) SEQ ID NO:10;
   (g) SEQ ID NO:11;
   (h) SEQ ID NO:12;
   (i) SEQ ID NO:13;
   (j) SEQ ID NO:14;
   (k) SEQ ID NO:15;
   (l) SEQ ID NO:16; and
   (m) SEQ ID NO:17;
   (vi) the at least one conjugate comprises at least one hemoglobin alpha chain subunit, and wherein the at least one hemoglobin alpha chain subunit comprises an αA19C modification and the further modifications αV1M and αL29F; and
   further comprises at least one further hemoglobin chain subunit wherein the at least one further hemoglobin chain subunit comprises at least one hemoglobin beta chain subunit, and wherein the at least one beta chain subunit comprises the modifications βC93A, βV1M, βV67F and βT84Y;
   (vii) the at least one conjugate comprises at least one hemoglobin alpha chain subunit, and wherein the at least one hemoglobin alpha chain subunit comprises an αA19C modification; and
   further comprises at least one further hemoglobin chain subunit, and wherein the at least one further hemoglobin chain subunit comprises at least one hemoglobin gamma chain subunit, and wherein the at least one hemoglobin gamma chain subunit comprises the modification γC93A; or
   (viii) the at least one conjugate comprises at least one hemoglobin alpha chain subunit, and wherein the at least one hemoglobin alpha chain subunit comprises an αA19C modification and the further modifications αV1M and αL29F; and
   further comprises at least one further hemoglobin chain subunit, wherein the at least one further hemoglobin chain subunit comprises at least one hemoglobin gamma chain subunit, and wherein the at least one hemoglobin gamma chain subunit comprises the modifications γC93A, γG1M, γV67F and γT84Y.

15. The recombinant modified multimeric protein according to claim 10, wherein the multimer is cross-linked.

16. A composition comprising a conjugate according to claim 1 or a recombinant modified multimeric protein according to claim 10 and a pharmaceutically acceptable carrier or diluent.

17. The composition according to claim 16, further comprising at least one reductant, optionally wherein:
   (i) the at least one reductant is ascorbate; or
   (ii) the composition is a blood substitute composition.

18. A method of treating and/or preventing ischemia and/or hypoxia, the method comprising administering a pharmaceutically effective amount of a pharmaceutical composition according to claim 16.

19. The conjugate according to claim 1, wherein:
   (i) the polymeric moiety is a maleimide functionalized polyethylene glycol; or
   (ii) the polymeric moiety is a polyethylene glycol having a molecular weight between 15000 to 25000 Da.

* * * * *

UNITED STATES PATENT AND TRADEMARK OFFICE
CERTIFICATE OF CORRECTION

| | |
|---|---|
| PATENT NO. | : 11,529,421 B2 |
| APPLICATION NO. | : 15/733287 |
| DATED | : December 20, 2022 |
| INVENTOR(S) | : Cooper et al. |

It is certified that error appears in the above-identified patent and that said Letters Patent is hereby corrected as shown below:

In the Claims

In Column 60, Line 24, in Claim 7, after "the", insert --at--

In Column 61, Line 58, in Claim 14, after "NO:8", insert --;--

In Column 61, Line 59, in Claim 14, after "NO:9", insert --;--

Signed and Sealed this
Third Day of September, 2024

*Katherine Kelly Vidal*

Katherine Kelly Vidal
*Director of the United States Patent and Trademark Office*